US012465512B2

(12) United States Patent
Snow et al.

(10) Patent No.: US 12,465,512 B2
(45) Date of Patent: Nov. 11, 2025

(54) ORTHOPEDIC BRACE WITH CUSTOM-FITTED FRAMEWORK OF LIGHT-CURABLE MATERIAL

(71) Applicant: Arctic Bracing LLC, McKinney, TX (US)

(72) Inventors: Brian Snow, Fairview, TX (US); Jeff King, Melissa, TX (US); Brian Lewis Hambrick, McKinney, TX (US)

(73) Assignee: Arctic Bracing LLC, McKinney, TX (US)

( * ) Notice: Subject to any disclaimer, the term of this patent is extended or adjusted under 35 U.S.C. 154(b) by 421 days.

(21) Appl. No.: 17/800,485

(22) PCT Filed: Feb. 24, 2021

(86) PCT No.: PCT/US2021/019434

§ 371 (c)(1),
(2) Date: Aug. 17, 2022

(87) PCT Pub. No.: WO2021/173686

PCT Pub. Date: Sep. 2, 2021

(65) Prior Publication Data

US 2023/0148303 A1 May 11, 2023

Related U.S. Application Data

(60) Provisional application No. 62/980,934, filed on Feb. 24, 2020.

(51) Int. Cl.
*A61F 5/01* (2006.01)
*A61F 5/32* (2006.01)

(52) U.S. Cl.
CPC .............. *A61F 5/0125* (2013.01); *A61F 5/32* (2013.01); *A61F 2005/0132* (2013.01)

(58) Field of Classification Search
CPC .... A61F 5/05825; A61F 13/04; A61F 5/0125; A61F 5/32; A61F 2005/0132;
(Continued)

(56) References Cited

U.S. PATENT DOCUMENTS 4,672,955 A * 6/1987 Cooper ................. A61F 5/0125 602/5
5,042,464 A * 8/1991 Skwor ........................ C08J 9/42 602/26
(Continued)

FOREIGN PATENT DOCUMENTS

WO 2019175589 A1 9/2019

OTHER PUBLICATIONS

PCT International Search Report and Written Opinion issued in PCT/US2021/019434, dated Jun. 3, 2021; 17 pages.
(Continued)

*Primary Examiner* — Ophelia A Hawthorne
(74) *Attorney, Agent, or Firm* — Alliance IP, LLC

(57) ABSTRACT

An orthopedic brace is provided that includes one or more pad plates formed of a light-curable material and a hinge comprising one or more hinge framework elements connected to the one or more pad plates. The pad plates may include an elastomeric shell to contain the light-curable material. A rigid attachment member may be coupled to the elastomeric shell to couple to the hinge framework element.

19 Claims, 26 Drawing Sheets

(58) Field of Classification Search
CPC ...... A61F 5/0102; A61F 5/0123; A61F 5/013; A61F 5/0585; A61F 5/05858; A61F 5/0118; A61F 5/0106; A61F 5/0111; A61F 5/0116; A61L 15/12; A61G 13/123
See application file for complete search history.

(56) References Cited

U.S. PATENT DOCUMENTS

| | | | | |
|---|---|---|---|---|
| 5,195,945 | A | 3/1993 | Sandvig et al. | |
| 8,034,010 | B1 * | 10/2011 | Sauer .................. | A41D 13/065 2/24 |
| 2009/0264551 | A1 | 10/2009 | Nakasugi et al. | |
| 2016/0270945 | A1 | 9/2016 | Tomblin et al. | |
| 2017/0079830 | A1 | 3/2017 | Chhatrala et al. | |
| 2017/0297278 | A1 | 10/2017 | Lecursi et al. | |

OTHER PUBLICATIONS

EPO European Extended Search Report in EP Application Serial No. 21759522.2 mailed on May 3, 2024, 10 pages.
International Preliminary Report on Patentability received for PCT Patent Application No. PCT/US2021/019434, mailed on Sep. 9, 2022, 10 pages.

* cited by examiner

ORTHOPEDIC BRACE WITH CUSTOM-FITTED FRAMEWORK OF LIGHT-CURABLE MATERIAL

RELATED APPLICATIONS

This Application is a national phase filing under 35 U.S.C. § 371 of International Application No. PCT/US2021/019434, filed Feb. 24, 2021, which claims benefit to U.S. Provisional Patent Application Ser. No. 62/980,934, filed Feb. 24, 2020, the disclosures of which are incorporated by reference herein in their entirety.

BACKGROUND

The present disclosure relates in general to the field of orthopedic devices, and more specifically, to customizable orthopedic brace devices.

Orthoses, or orthopedic devices, serve as medical aids for stabilizing, relieving stress, immobilization and, in particular, for guiding or correcting a patient's limbs and joints, including the corresponding muscle tissue, ligaments, and bone structures. Generally, mechanical stabilization and guiding or correction is achieved in particular by mechanically rigid stabilizing elements in the orthopedic devices, which are brought into firm mechanical contact with the body such that supporting forces can be absorbed or correction forces can be exerted. Mechanical joint rails and bridges are often employed, in connection with rigid frames or other structure to provide such protection, correction, and guidance. A range of orthopedic devices have been developed for various parts of the human body (as well as for veterinary uses), including braces for knees, hips, spine, elbow, wrists, ankles, etc.

BRIEF DESCRIPTION OF THE DRAWINGS

Like reference numbers and designations in the various drawings indicate like elements.

DETAILED DESCRIPTION

An improved orthopedic brace is provided in the present disclosure utilizing a curable resin, cured using ultraviolet light (UV), to custom fit one or more pad frameworks, or pad plates, to the contours of a patient. The UV-curable resin may interface with and connect to non-resin elements of the brace, including framework of one or more hinge elements made of materials other than the UV-curable resin. Through the UV-curable resin-based pad plates, the brace may be custom molded to each patient. This allows a more comfortable fit customized to each patient's individual size, shape and degree of deformity secondary to the arthritic condition. By applying and molding custom framework to each patient, the patient's native deformity becomes the brace's shape, for a more natural and comfortable fit. This also sets the brace at the starting anatomy of the patient's native deformity, thus allowing more reproducible degrees of unloading in spite of native *Varus* or valgus alignment.

Turning to FIGS. 1A-1D, views of an example orthopedic brace (e.g., a knee brace, hip brace, elbow brace, shoulder brace, ankle brace, etc.) are shown, including one or more plates (e.g., 105, 110, 115) coupled to one or more hinges (e.g., 120). One or more of the plate pieces may be adapted to contact or otherwise engage the body of a patient, either directly or via padding dispositioned (e.g., connected to the plate) between the plate and the body of the patient. One or more of the plates (e.g., 105, 110, 115) may be constructed, at least in part, from a UV-curable resin material, which may be formed around the body part(s) to be contacted or aligned with the plate (and corresponding padding) while in a liquid or gel state and then hardened by applying ultraviolet light to the resin material to permanently set the plate to customize the plate to the contours of the patient's body. Other elements of the brace, such as components of the hinge, may be formed of materials other than UV-curable resin material, and may be joined (e.g., permanently) to the one or more of the UV-curable resin-based plates during the curing process, such as detailed herein.

Figure 1A:
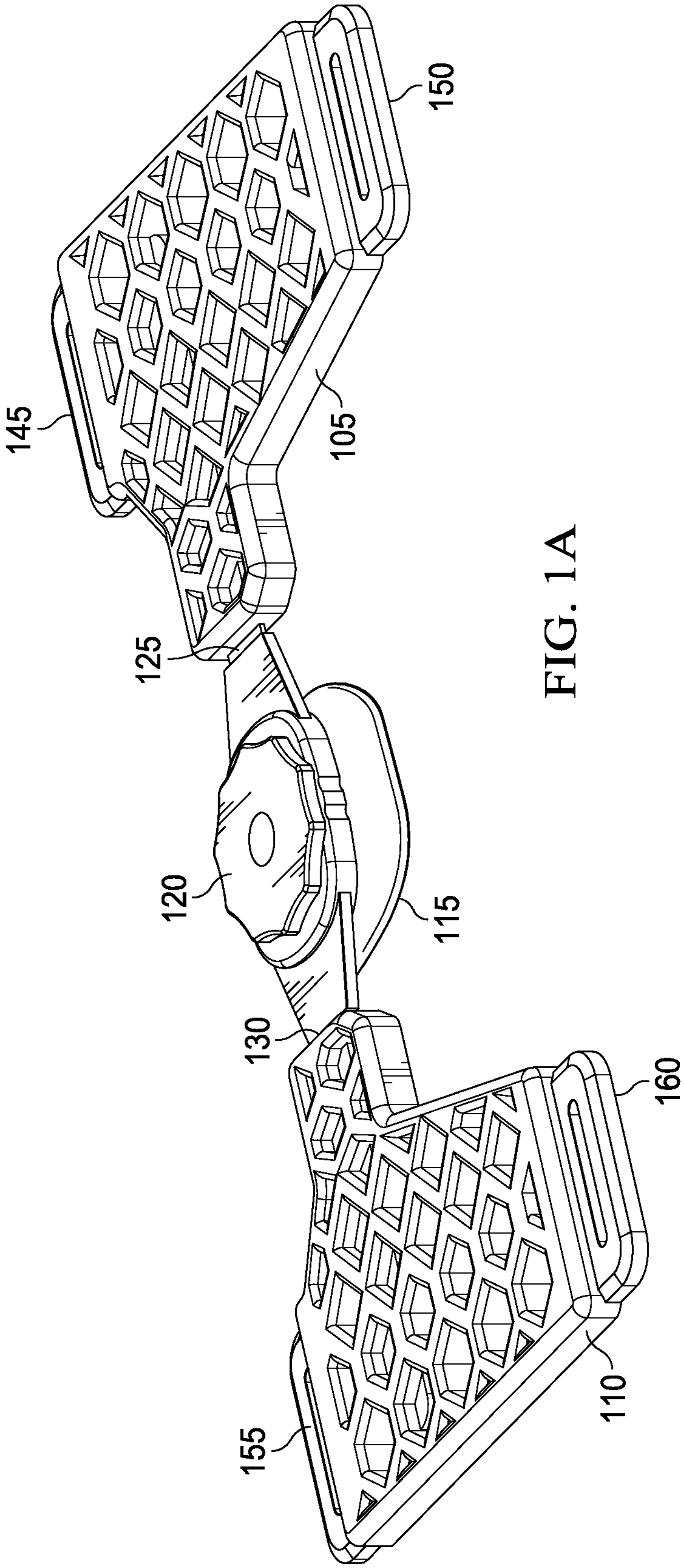
FIGS. 1A-1D show views of an example brace device in accordance with at least one embodiment.
Figure 1B:
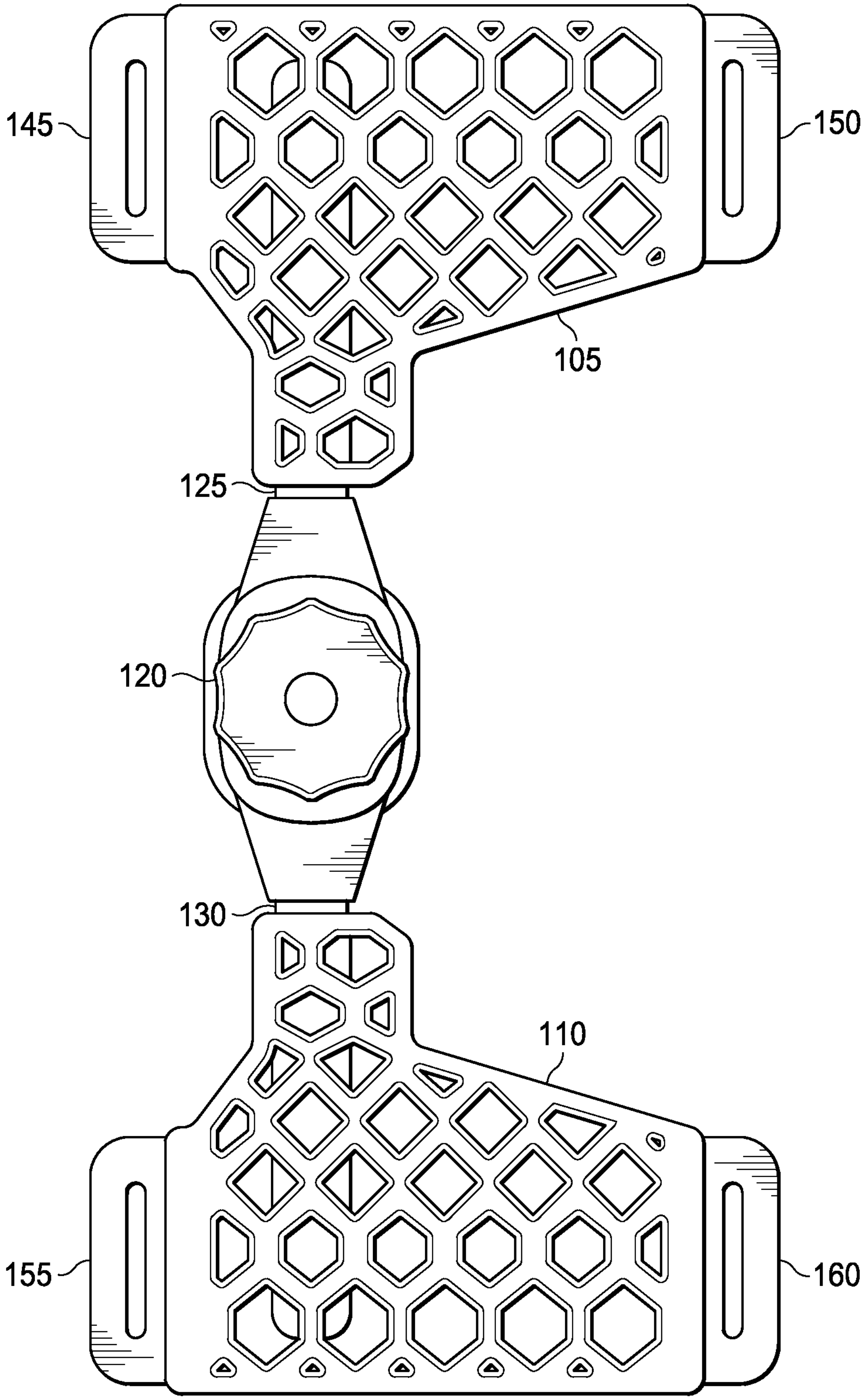
Figure 1C:
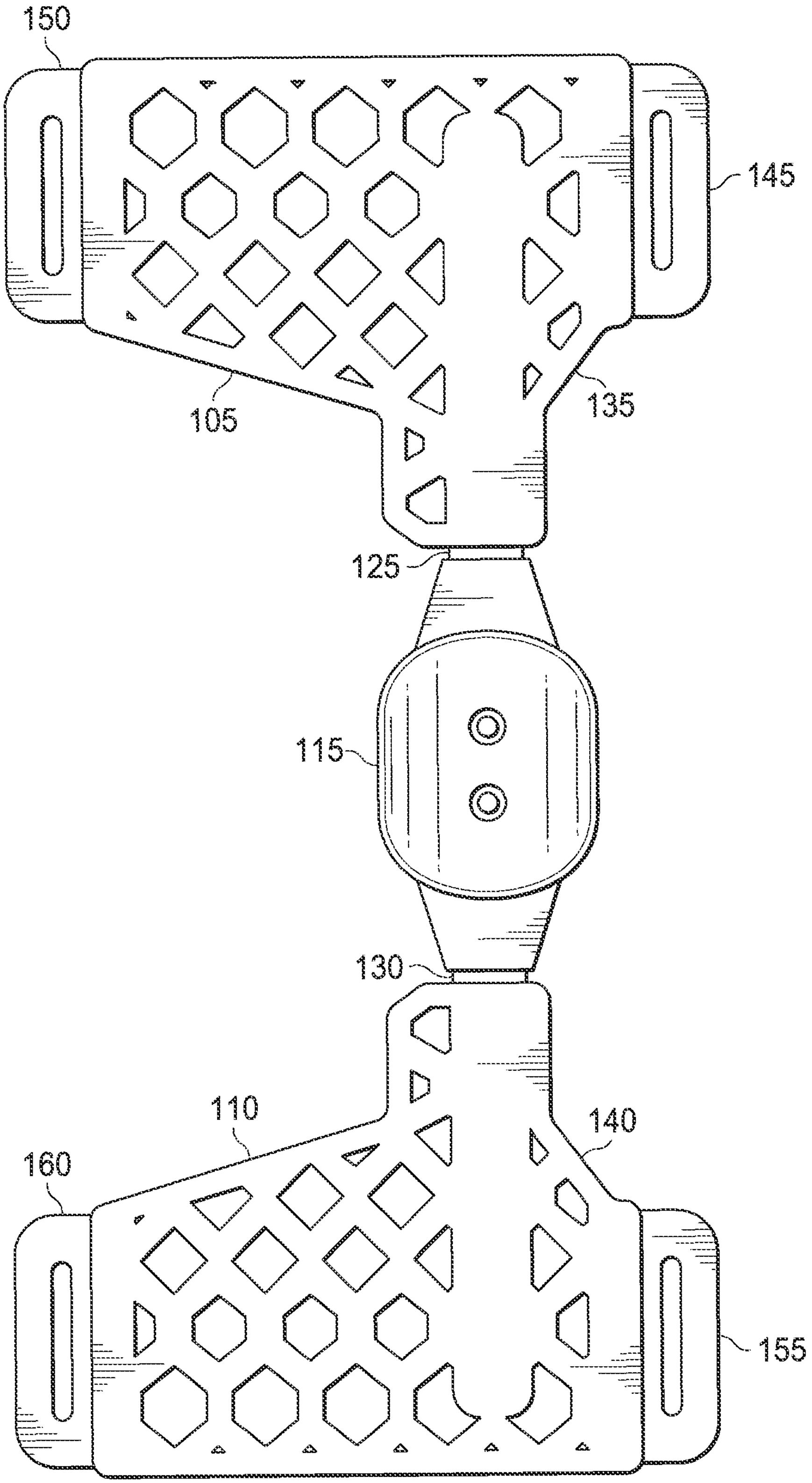
Figure 1D:
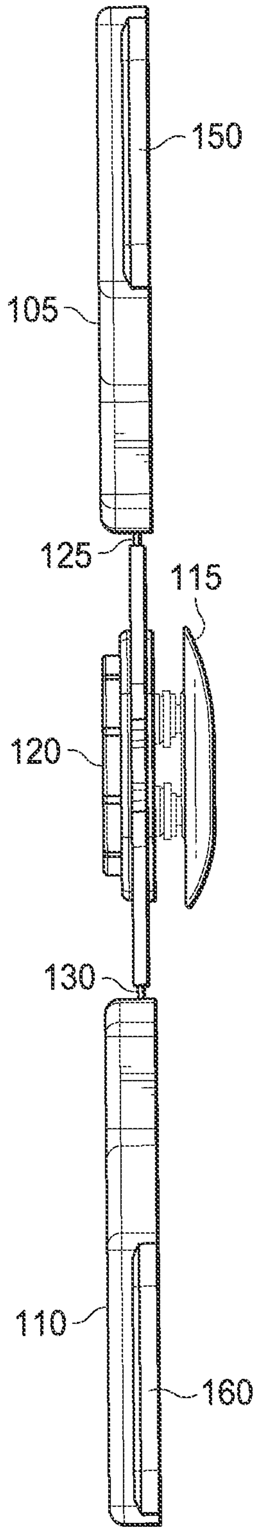

FIG. 1A shows a perspective view of an example brace device, including two pad plates (e.g., 105, 110) composed of a UV-curable resin material, attached to a hinge component 120 via two respective hinge frame members 125, 130 made of a rigid material such as aircraft grade aluminum, stainless steel, carbon fiber, plastic, or another (non-UV-curable resin material). Another pad plate (e.g., 110) may be provided on the hinge component 120 (e.g., via telescoping attachment), such as an unloader plate (with corresponding padding), which may also be constructed from a UV-curable resin or pre-formed (e.g., not custom fabricated) from another material (e.g., a plastic), among other example implementations. An example brace device may additionally include attachment mechanisms to secure the brace device to a limb or other body part of a patient which is to be treated or otherwise corresponds to the brace. For instance, one or more straps may be included with the brace device to secure the brace device to a body of a patient. Accordingly, in some implementations, an example brace device may include strap connectors (e.g., 145, 150, 155, 160) that include openings through which straps may be fed to couple to the pad plates (e.g., 105, 110) and enable the straps to be used to secure the brace device to a patient. FIG. 1B is an exterior side view of the example brace device, showing a side that faces away from the patient's body and is not in contact with the patient. FIG. 1C shows an interior side view of the brace device, showing the side opposite the exterior side with padding (e.g., 135, 140) disposed on the pad plates (e.g., 105, 110) to be brought into contact with the patient's body (e.g., the body parts corresponding to the brace's orthopedic purpose). FIG. 1D shows a front view of the example brace device.

Figure 2A:
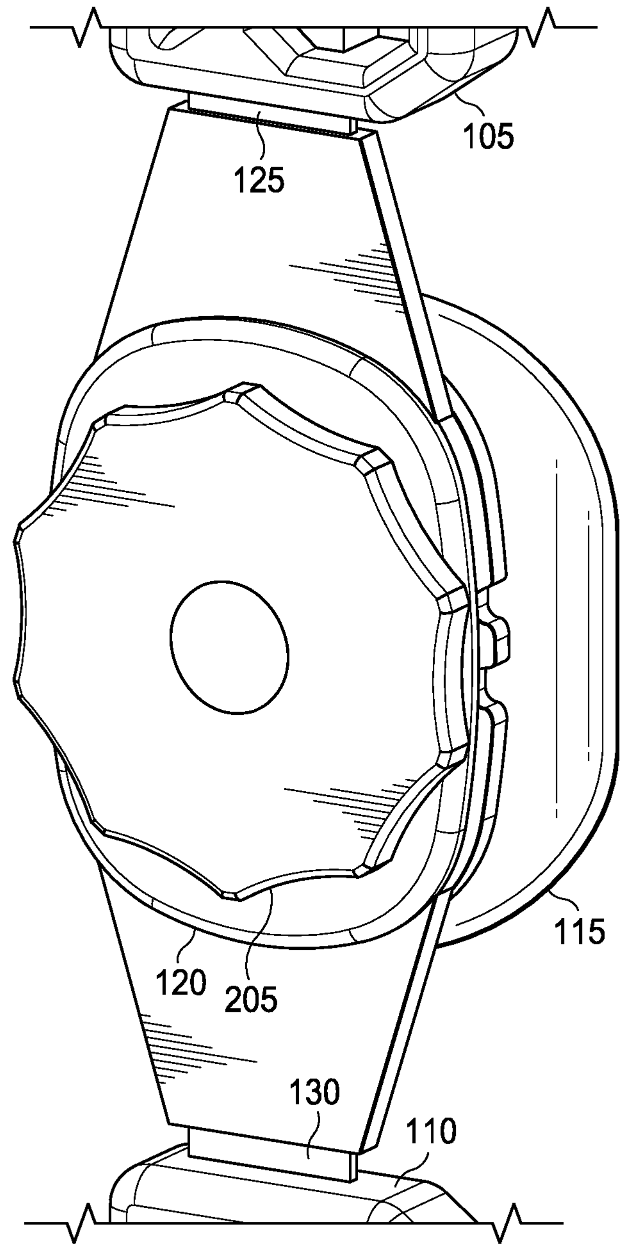
FIGS. 2A-2B show close up views of an example hinge element of an example brace device in accordance with at least one embodiment.
Figure 2B:
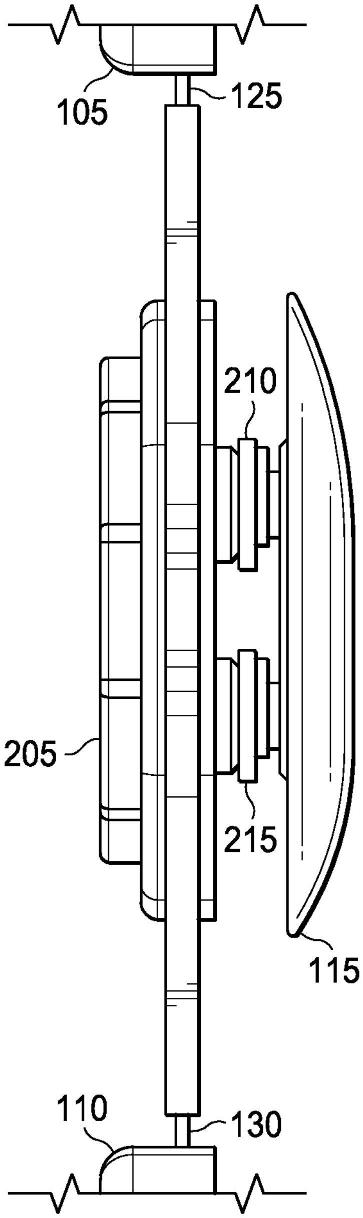

Turning to FIGS. 2A-2B, close-up views are shown of an example hinge element 120, permanently secured to custom pad plates formed from a UV-curable resin material. FIG. 2A shows a perspective view of the hinge element 120 and FIG. 2B shows a front view of the hinge element 120. In this example, the hinge enables movement (e.g., flexion/extension, abduction, adduction, rotation, circumduction, etc.) and, in some cases, enforces limitations on joint movement (e.g., limiting the range of joint movement). In the example of FIGS. 2A-2B, a Varus/valgus Allen telescoping mechanism is proved to enable enhanced degrees of correction to the patient's native neutral alignment. In this example, aircraft grade aluminum is utilized in framework elements 125, 130, which are to connect to pad plates 105, 110. A telescoping Varus/valgus unloading dial 205 is provided, which may be rotated to adjust the position of unloader plate 115 (through telescoping transitional bolts 210, 215), which may be provided with a pad (not shown) to adjustably contact the joint (e.g., knee) of the patient. In this example, the hinge is implemented as a two-panel hinge with flexion/extension stop insert elements to enable the range of motion to be controllably limited in correspondence with the determined treatment of the patient.

As discussed above, a UV-curable resin material may be utilized to construct custom-fit plates contoured to the anatomy of specific patients. Such materials may be selected from any composite material that is in a liquid or gel form until polymerized and cured by the energy radiated from ultraviolet irradiation devices. Light-curable resin materials, as discussed herein, may include oligomers, monomers, photo-polymerization initiators, coinitiators (e.g. spectral sensitizer, reducing agents, etc.), and various additives such as stabilizers, antioxidants, plasticizers, and pigments. Light-curable resin materials include acrylate radical polymerization materials (e.g., polyester and epoxy resins, aliphatic and aromatic urethanes, silicones and polyethers) and epoxy cationic polymerization materials, among other examples. The material may be injected or infused within a flexible bladder or mold (or "shell"), to contain the liquid or gel material and enable forming of the material around the body part of a patient prior to curing. The materials may be a low viscosity epoxy material that includes epoxy resins, acrylate fillers and activators, polyurethane or any combination thereof. In the case of light-curable materials, a light curable composite epoxy resin can used. Through light curing techniques, the material may be cured to permanently adopt a particular shape (e.g., corresponding to a body part around which the flexible mold (containing the material) is wrapped) by exposing the flexible (and at least partially transparent) mold and material to light. In some implementations, the light-curable material may include epoxy mixed with filler material such as nanofibers to increase strength of cured material. In one implementation, the light-curable material can be a monomer material which is selected to give adequate strengthening for immobilization. Material will be provided as two premix forms which will be mixed prior to being injected or infused into the flexible mold or bladder. In some examples, polymerization of the material may start within 5-10 minutes of exposure to light and can give basic hardening strength within 15 minutes.

Figure 3A:
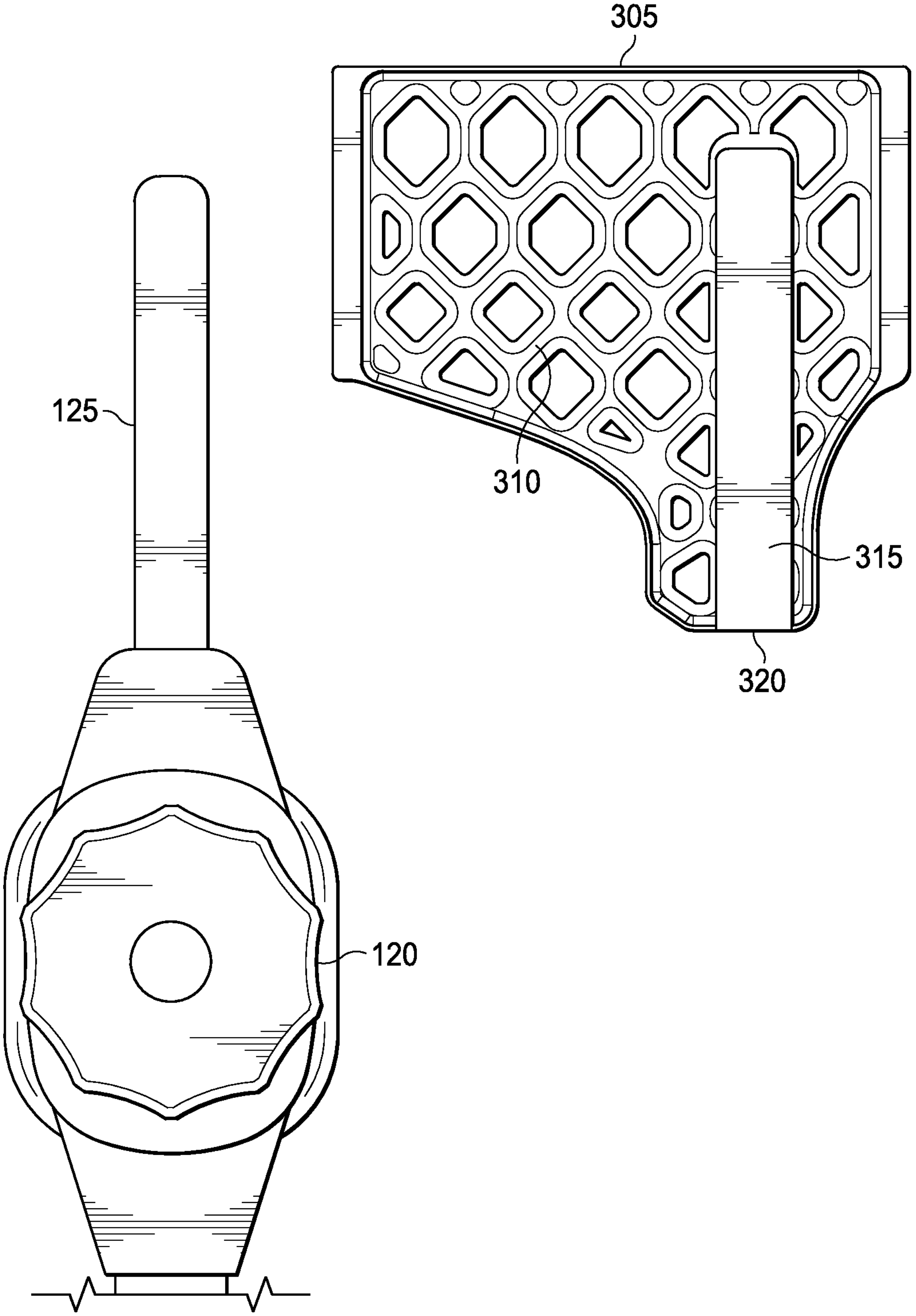
FIGS. 3A-3B are diagrams showing the example assembly of a customized brace device utilizing a light-curable resin in accordance with at least one embodiment.
Figure 3B:
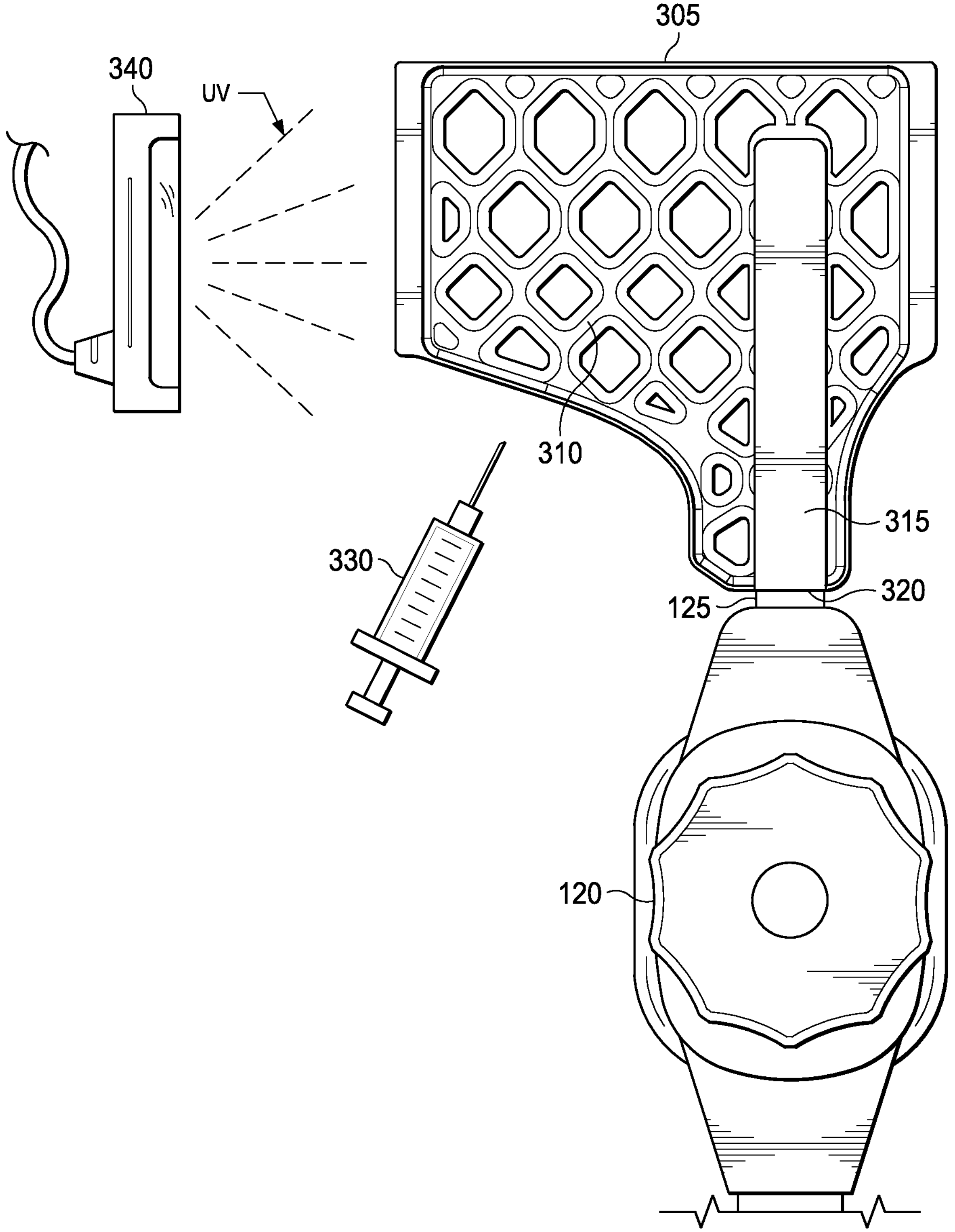
Figure 4A:
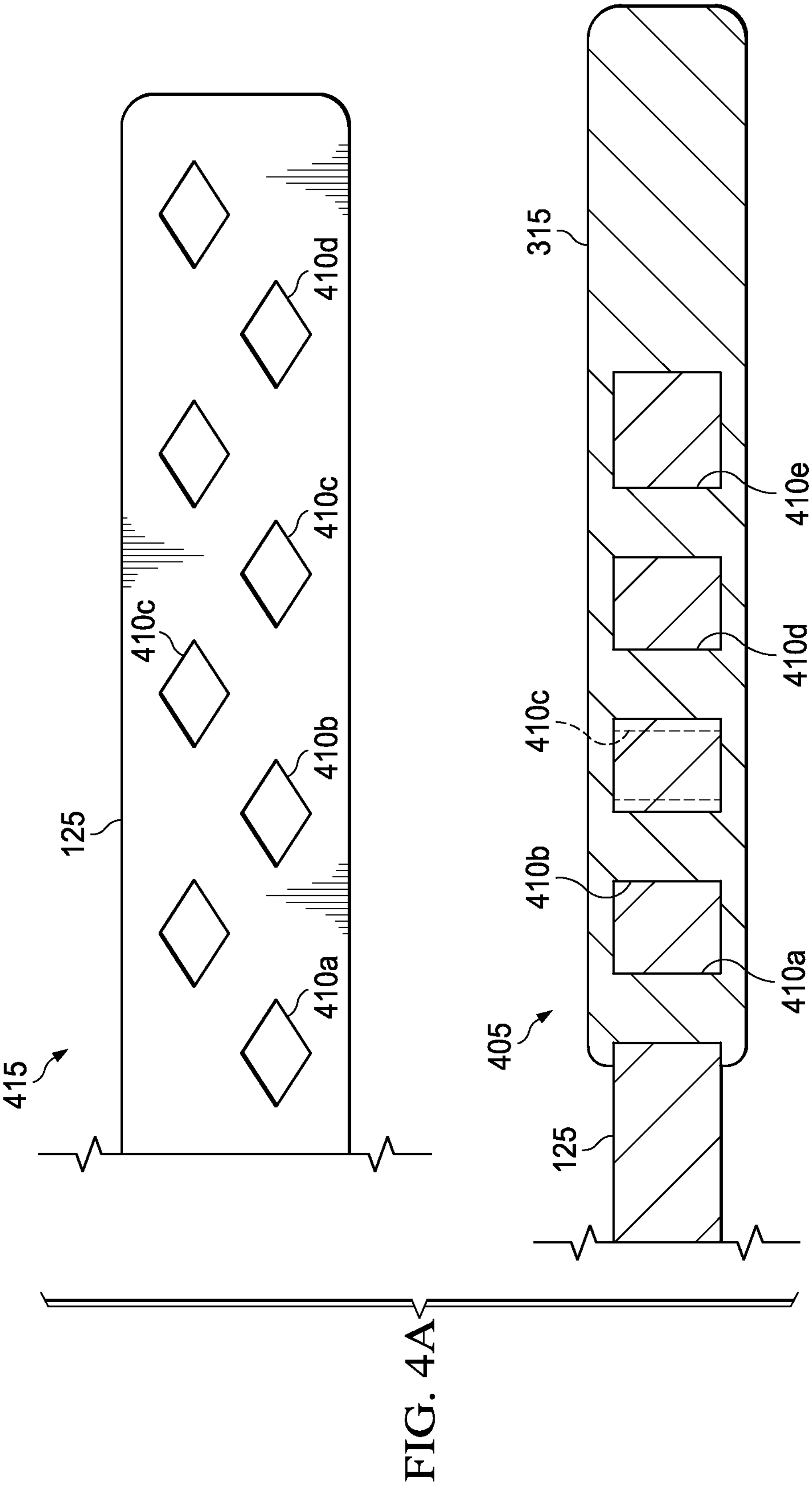
FIGS. 4A-4E are diagrams showing example hinge frame member to connect with a cured resin pad plate of an example brace device in accordance with at least one embodiment.
Figure 4B:
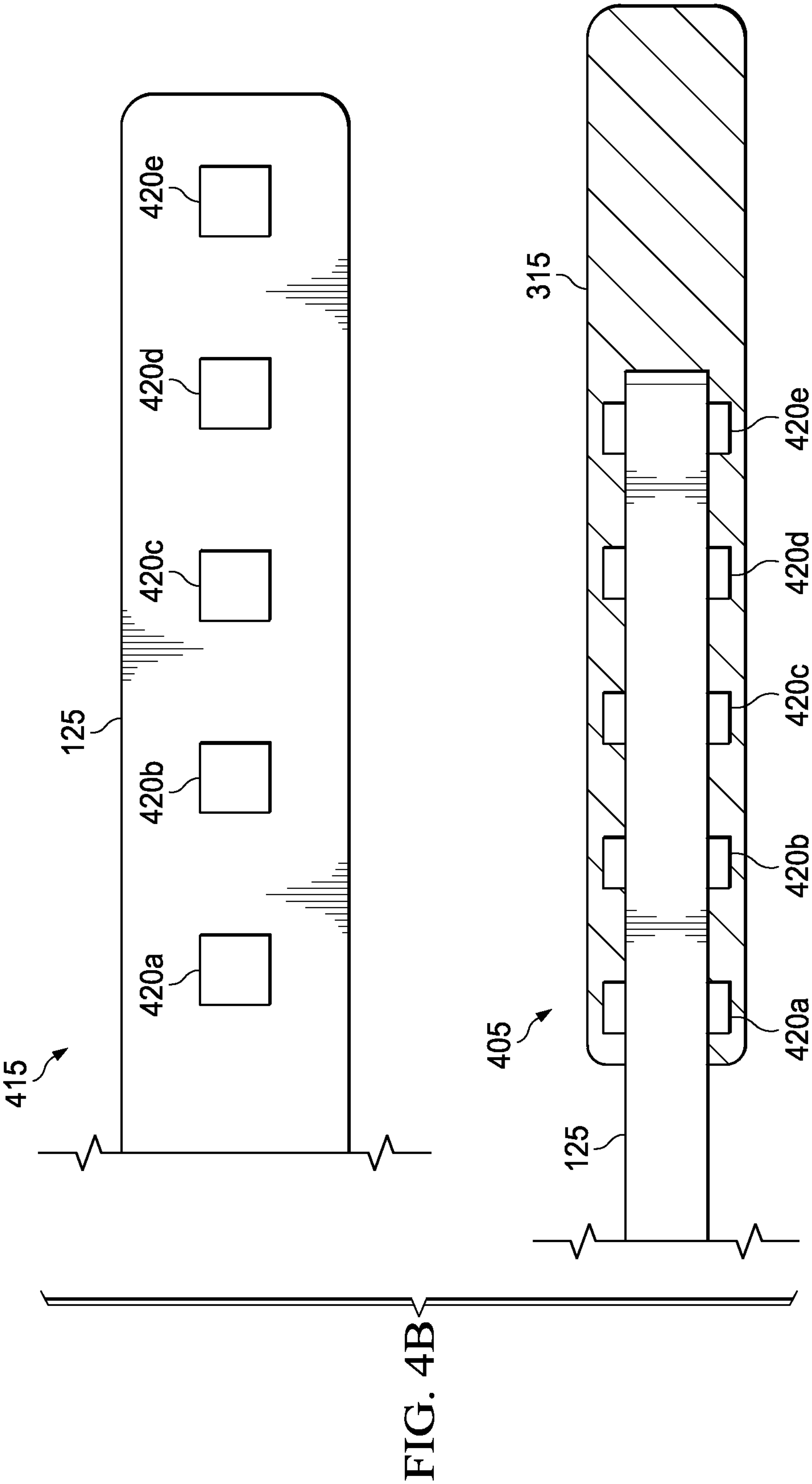
Figure 4C:
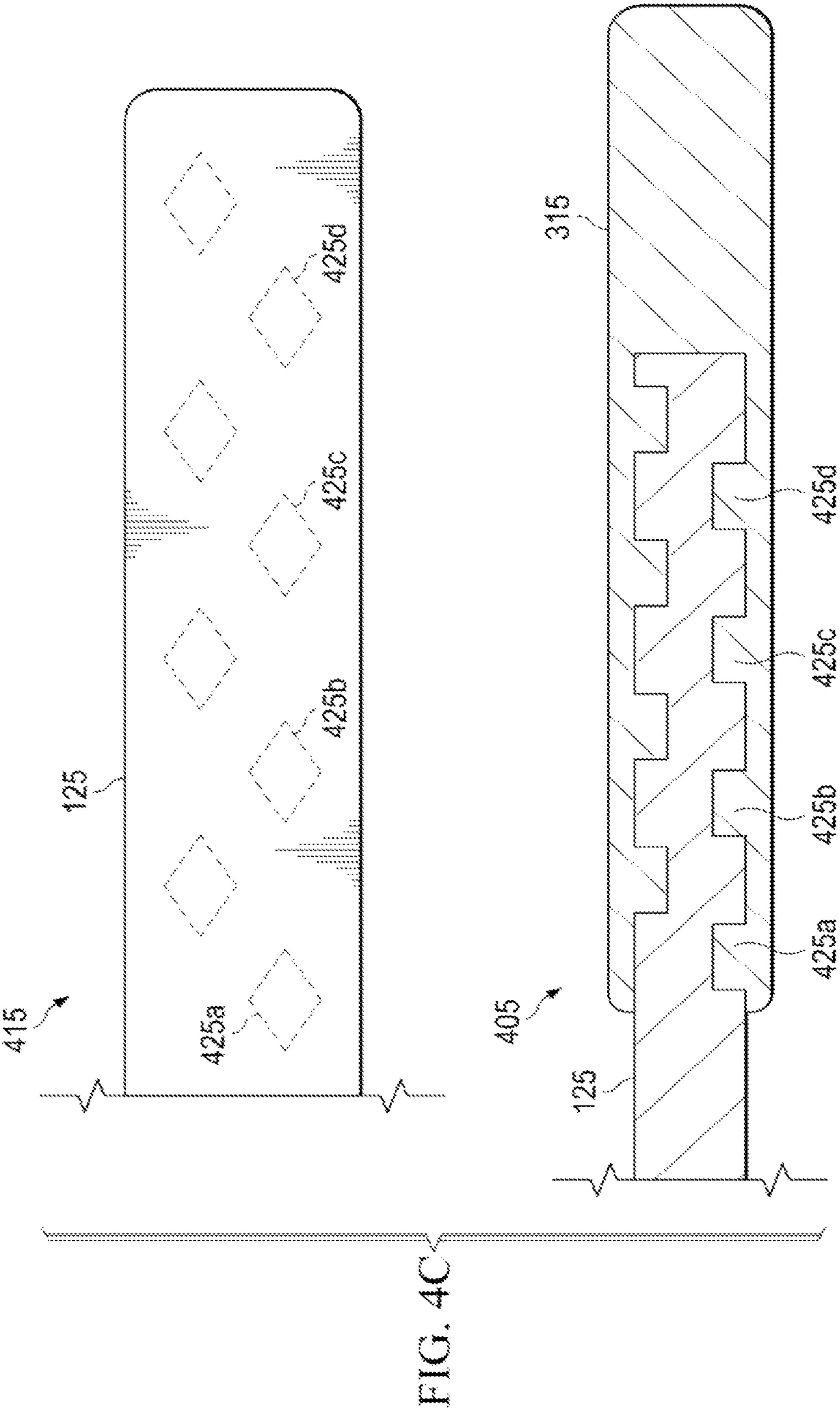
Figure 4D:
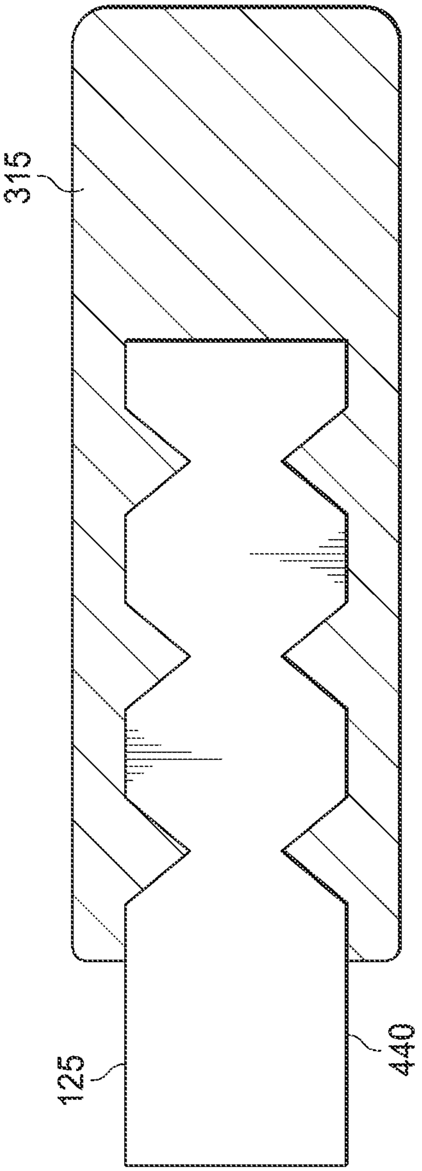
Figure 4E:
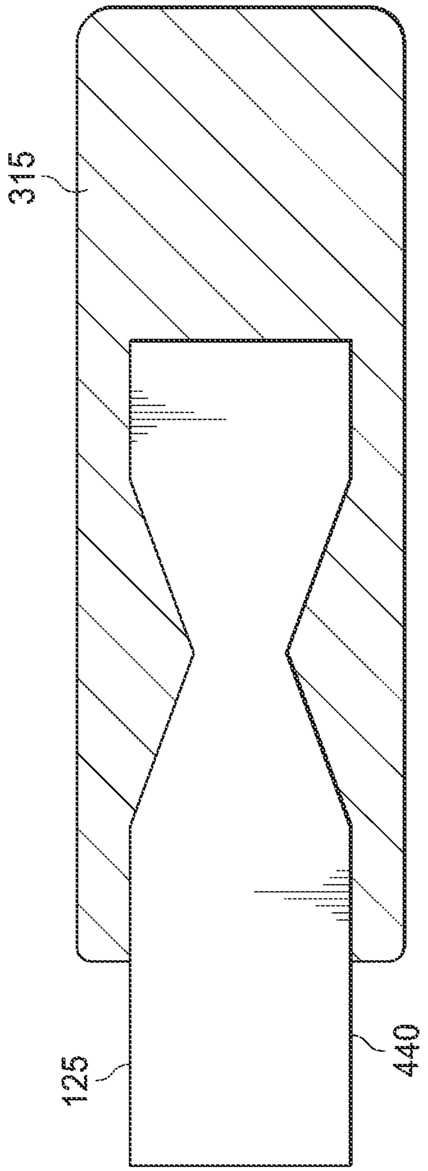

Turning to FIGS. 3A-3B, diagrams show the example assembly of a customized brace device utilizing a light-curable resin. A flexible bladder or mold (e.g., 305) may be provided, which include one or more hollow, tubular cavities adapted to be filled with and contain the light-curable material in its liquid or gel form. For instance, in the example illustrated in FIG. 3A, a network of tubular cavities (e.g., 310) may be provided to be filled with the light-curable material and then sealed to contain the material. This may facilitate the construction of a pad plate with openings to allow increased breathability of the brace and/or to facilitate observation (through the holes formed in the plate by the network of tubular channels) by a medical professional of the body beneath the plate (e.g., to monitor normal circulation or swelling around the site of a corresponding injury, surgical scar, etc.). A flexible mold 305 may additional include an opening or sheath (e.g., 315) formed to enable a frame member (e.g., 125) of a hinge element 120 of a brace to be inserted into the flexible mold.

The general size and shape of pad plates constructed from light-curable materials is based on the size and shape of the flexible mold 305. Accordingly, different sizes and shapes of molds may be provided to accommodate patients of varying ages/sizes and different types of orthopedic braces. The flexible mold 305 may be constructed of material that is at least partially transparent so as to allow light to penetrate the surface of the mold 315 and cure the light-curable material contained within the channels, bladders, etc. of the mold. In some implementations, the flexible mold may be composed of an at least semi-transparent, flexible, elastomeric materials, such as a silicon, silicon rubber, latex rubber, synthetic rubber, or other material or combination thereof. The flexible nature of the material allows the mold to be wrapped, stretched, formed around a patient's limb (or other body part).

Turning to FIG. 3B, hinge frame element 120 is inserted into an opening 320 of the sheath 315 of flexible pad plate mold 305. The opening 320 may be sealed to enable light-curable material to be injected or otherwise infused into the remaining volume of the sheath (around the hinge frame element 120. In some implementations, the dimensions and elastomeric qualities of the opening 320 may result in the opening 320 snugly wrapping around the hinge frame element 120 to thereby form a seal sufficient to prevent the escape of light-curable material (after infusion) from the sheath 315. In other instances, a tape, glue, or other sealant may be provided at the opening 320 to prevent the escape of material from the sheath 315 portion of mold 305. Similarly, the material may be injected within the internal channels (e.g., 310) of the body of the mold 305 to infuse the cavities of the mold with the light-curable material. In some implementations, the cavities formed in the body of the mold and the sheath may be fluidically connected, such that infusion of the material in one cavity causes other connected cavities to be filled with the material. In other instances, the mold may be composed of two or more separate cavities, which are to be separates filled. For instance, cavities 310 may be separate from the cavity formed by sheath 315 and the same may be filled separately (e.g., in two or more infusion steps). In some implementations, the cavities 310 may be prefilled within the mold 305 with light-curable material (e.g., 330), merely awaiting insertion of a hinge frame member (e.g., 125) into the sheath 315 portion and then infusion of the light-curable material within the sheath cavity (also containing the inserted high frame member).

In some implementations, infusion of light-curable material (in its liquid or gel form) within the internal channels of a flexible brace plate mold (e.g., 305) may be performed utilizing a syringe (e.g., 330) or other pump device (e.g., electrically or mechanically powered) to pump the light-curable material into the mold 305. Light (e.g., 340) may then be applied to the mold to cure the material within the cavities of the mold and set the shape of the mold (and internal material) to conform to the body of a specific patient. In some implementations, while the mold may be transparent, a removable covering or layer may be provided on the exterior of the mold to protect light-curable material within from being prematurely exposed to light and cured. In such examples, the covering may be removed to enable light 340 exposure to the mold 305 and curing of the internal light-curable material. For instance, the mold infused with the material may be wrapped around a leg (or other body part) of a patient under the supervision of a medical professional. When the mold is positioned as desired, light may be introduced to cause the material to cure and harden to permanently form the mold into a resulting pad plate of a brace. Additionally, curing of light-curable material within the mold also serves to harden material around frame members (e.g., 125) of a hinge 120 of the brace and cause the frame member 125 to be permanently secured to the resulting pad plate (formed using the mold 305).

To assist in securing such hinge frame members (e.g., 125) to the pad plate (and light curable material forming the pad plate), various geometries may be adopted in the hinge frame members (e.g., 125), such that when light-curable material surrounding the hinge frame member in the sheath 315 (when the hinge frame member is inserted within the sheath 315) is cured and hardens, the hinge frame member 125 is permanently fixed within the pad plate. For instance, the illustrations of FIGS. 4A-4E show example geometric features, which may be adopted in such hinge frame members to encourage connection with a cured resin pad plate of the brace. For instance, in FIG. 4A, a cross-sectional view 405 of the side of a hinge frame member 125 is shown inserted within a sheath 315 of a pad plate mold filled with a light-curable material. In this example, holes (e.g., 410*a-e*) may be bored or otherwise formed on the face of the hinge frame member (as shown in front view 415 of the hinge frame member when outside the sheath). Accordingly, when light curable material inserted into the sheath it may surround the exterior of the hinge frame member 125 and fill-in the holes (e.g., 410*a-e*) of the hinge frame member 125. Accordingly, when the material is cured (e.g., through exposure to UV light) the material surrounding and passing through the hinge frame member 125 (e.g., via holes 410*a-e*) hardens to permanently integrate the hinge frame member with the resulting pad plate. Indeed, other non-uniform surface elements, including protrusions, ridges, ribs, depressions, holes, angled or scalloped edges, and other nonuniformities may be included on hinge frame members 125 which are to attach to pad plates through curing of light-curable material making up the pad plate and surrounding the hinge frame member (e.g., when the member is inserted into a sheath of a mold used to construct the pad plate.

FIGS. 4B-4E show additional examples of various non-uniformities, which may be included on a hinge frame member to encourage the joining of a hinge component with one or more pad plates constructed from light-curable material(s). For instance, in FIG. 4B, protuberance, nodules, ribs, or other projections (e.g., 420*a-e*) may be included on an example hinge frame member 125 and may cause the hinge frame member to be permanently secured within light-curable material used to form a pad plate after curing of the material. In another example shown in FIG. 4C, rather than utilizing holes which entirely penetrate the hinge frame members, depressions (e.g., 425*a-d*) may be formed in the surface(s) of the hinge frame member 125. These depressions may be filled within the light-curable material (e.g., when the material is injected within a sheath containing the hinge frame member 125) and may harden during curing to secure the hinge frame member 125 within the resulting pad plate. In still other examples, such as in FIGS. 4D-4E, rather than (or in addition to) nonuniformities formed on the face (front) of hinge frame members (e.g., 125) as in the examples of FIGS. 4A-4C, nonuniformities may be formed on the edges or sides (e.g., 440) of the hinge frame members to enhance the connection between the hinge frame member and cured material surrounding the hinge frame member 125 and forming the pad plate. Indeed, a combination of different nonuniformities may be utilized to enhance the quality of the connection while preserving the structural integrity of the hinge frame member 125, including nonuniformities other than those explicitly illustrated in FIGS. 4A-4E, such as protuberances, depressions, edge geometries, and other non-uniformities which may encourage joining a hinge frame member made from one material (e.g., aluminum, steel, molded plastic, etc.) with a pad plate made from a different, light-curable material, such as discussed herein.

Figure 5:
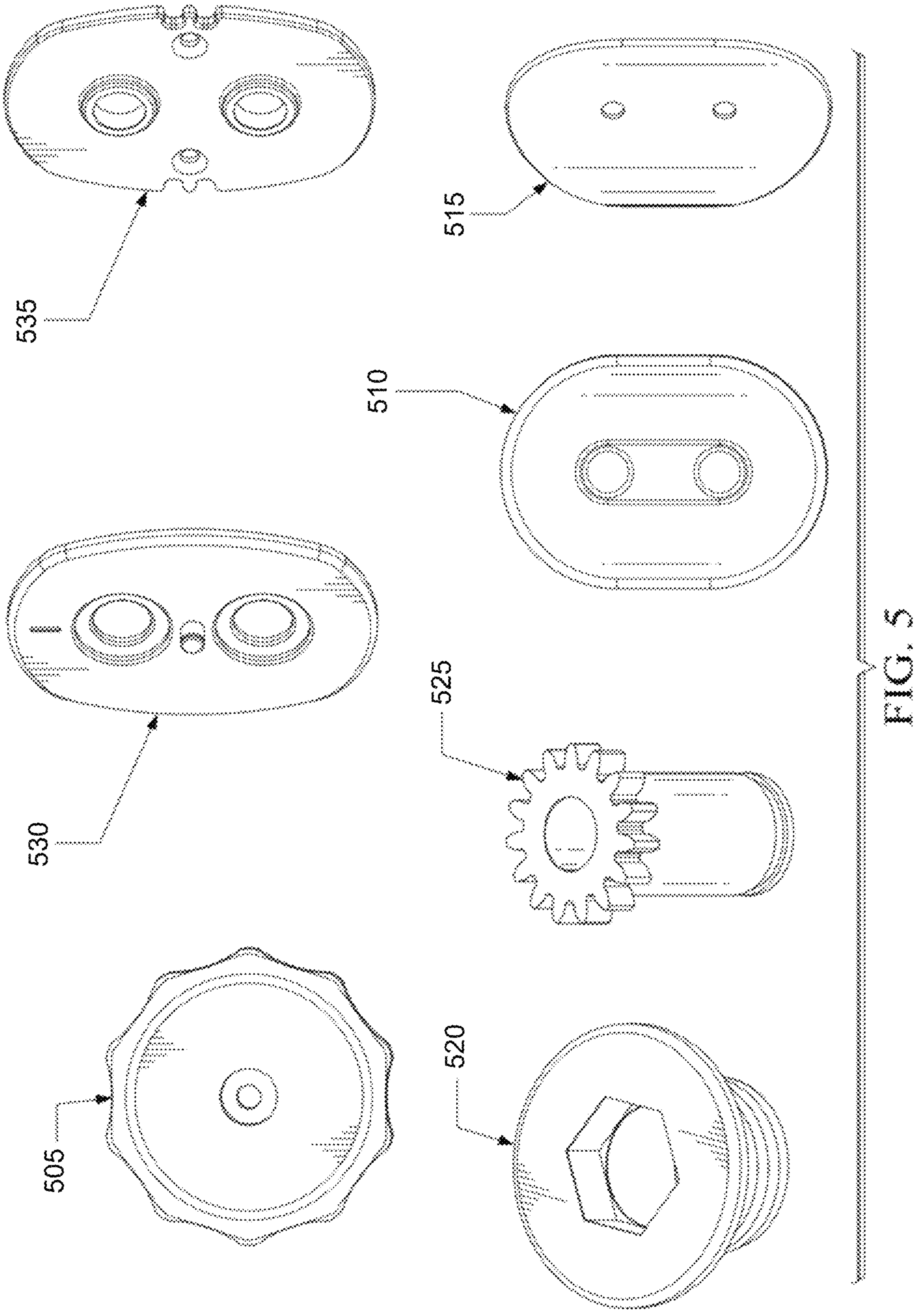
FIG. 5 is a diagram of components of an example hinge element of an example brace device in accordance with at least one embodiment.

FIG. 5 illustrates various components, which may be included within an example hinge connected to one or more pad plates constructed from light-curable material, such as discussed herein. For instance, a telescoping Varus/Valgus unloading dial 505 may be provided to manipulate placement of a corresponding unloading plates 510, 515 via telescoping transitional bolts 520, 525. Further, flexion/extension controls (or other controls) may be provided in the hinge to limit movement of a patient's joint when wearing the brace, such as through a two-panel hinge with flexion/extension stop insert(s) (e.g., 530, 535), among other examples.

Figure 6:
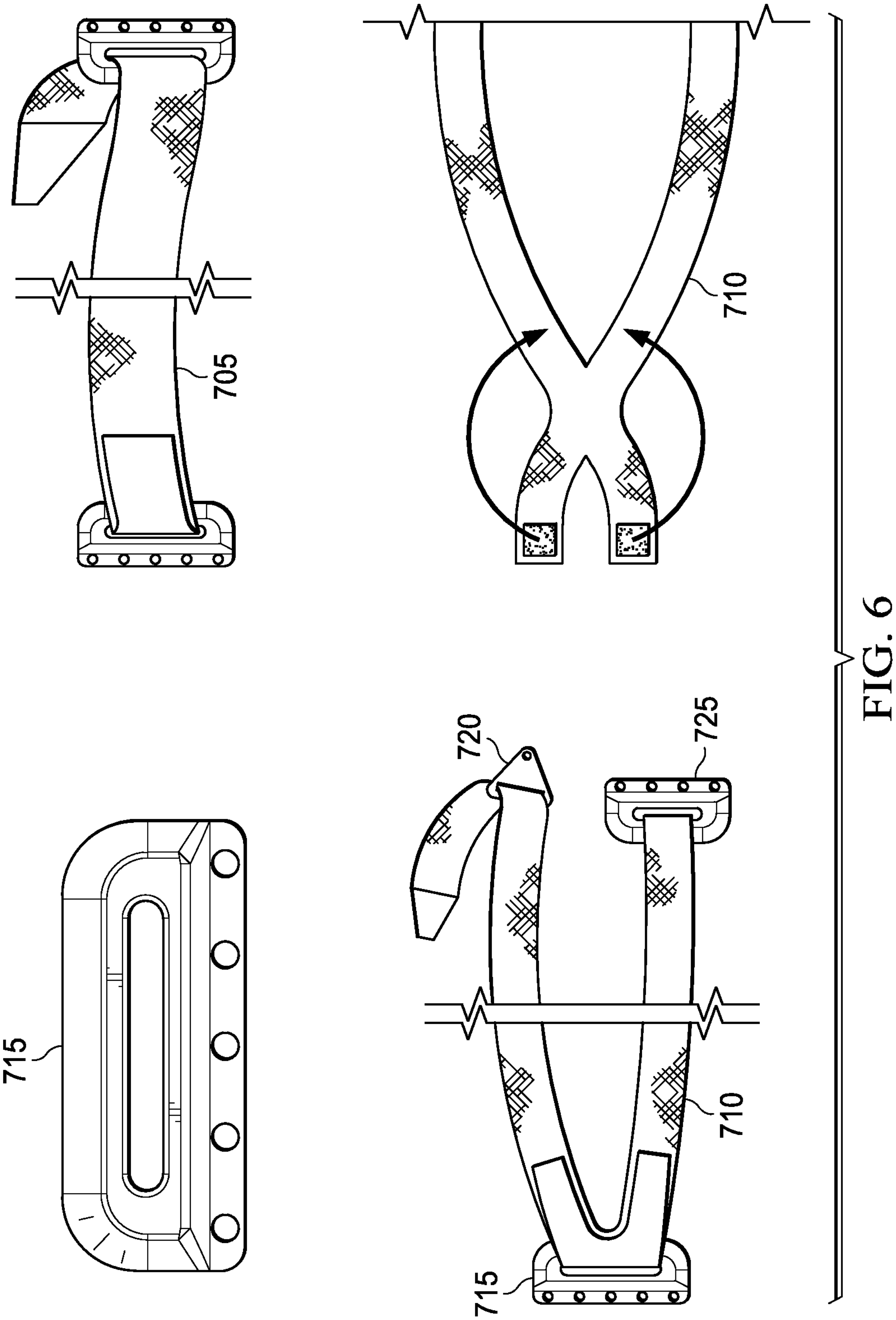
FIG. 6 illustrates example straps, which may be used in connection with an example brace device in accordance with at least one embodiment.

FIG. 6 illustrates example straps, which may be used in connection with an example brace device, of which at least a portion is constructed from light-curable material. For instance, strap connectors may be provided on the brace (e.g., on a pad constructed from light-curable material (e.g., formed from the light curable material or attached to the mold used to form a pad plate from light curable material, etc.). Such straps may be used to secure the finished brace device to a patient. Such straps may be further used during fitting and customization of the brace to a specific patient. For instance, upon infusing a pad plate mold with light-curable material, brace straps may be used to wrap the mold at least partially around a body part of the patient (e.g., under the direction of a medical professional). The hinge may be connected to the mold (e.g., such as shown in FIGS. 3A-3B)) and light may be applied to the hinge to cause the pad plates to cure into the shape of the body part to which the mold is strapped and permanently attach the pad plates to the hinge component (e.g., via corresponding hinge frame members).

In some implementations, hinge frame members may be attached to the mold (e.g., by curing light-curable material infused within a sheath of the mold adapted to accept the hinge frame member), followed by strapping the pad plate mold around the body of the patient and curing light-curable material infused within the pad plate mold to form customized brace device plates, among other examples.

Figure 7:
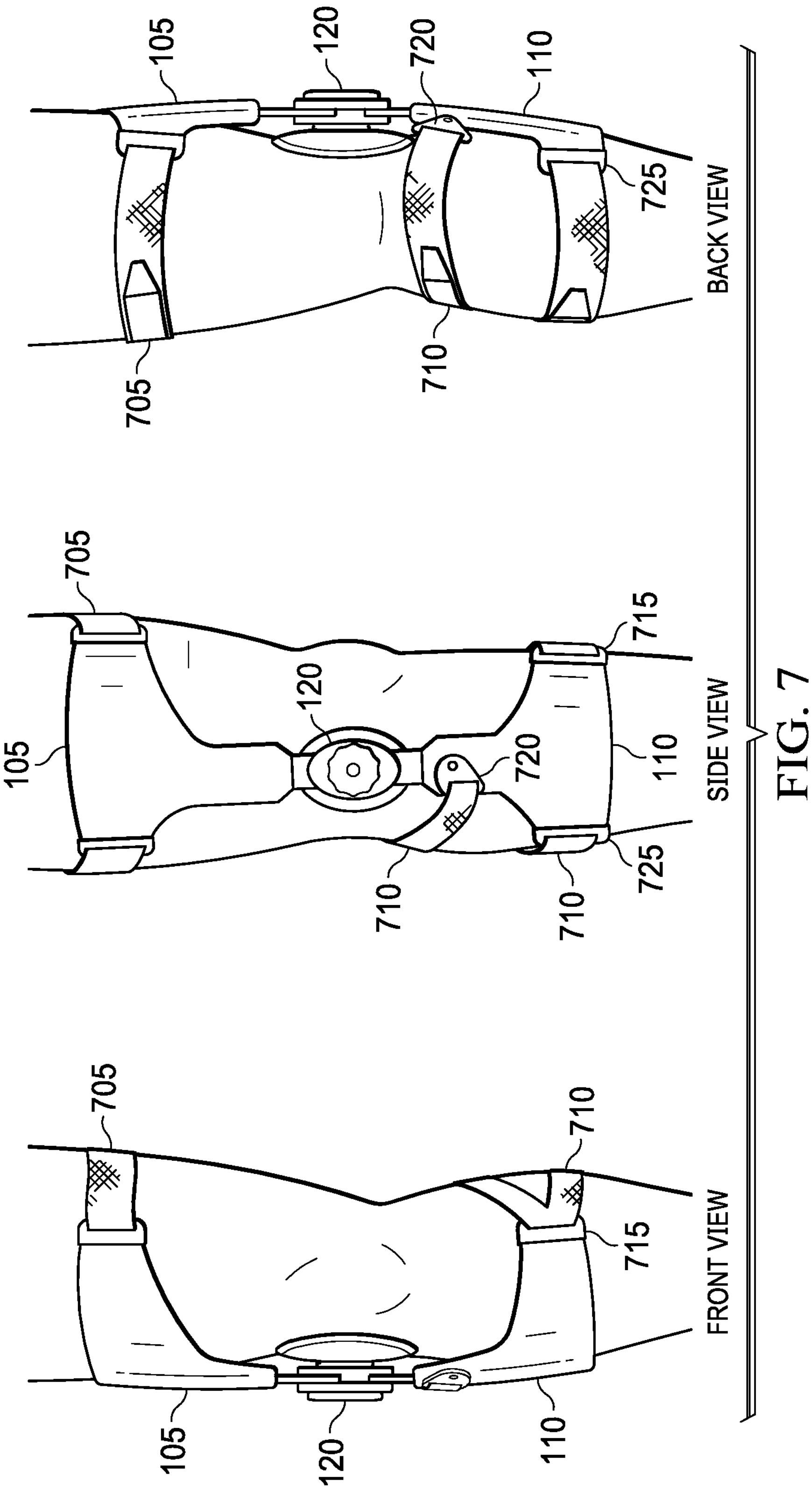
FIG. 7 illustrates front, side, and back views of an example knee brace in accordance with at least one embodiment.

Turning to FIG. 7, front, side, and back views of an example knee brace are shown, with pad plates (e.g., 105, 110) formed through curing of a light-curable resin and custom-fit to a particular patient. A hinge component framework, composed of a different material (e.g., aluminum, steel, etc.) may be integrally connected to the pad plates 105, 110 during curing of the light-curable material, such as discussed in association with FIGS. 3A-4E. Straps (e.g., 705, 710) may be used to couple the brace to a leg of a patient (e.g., at the thigh pad plate 105 and shin pad plate 110). In one example, the knee brace may have a connecting interface with customizable thigh strapping, with thigh and shin pad plates constructed from a curable UV resin and integrally connected (during curing) with an aircraft aluminum framework of a hinge. In one example the aircraft aluminum framing may have a gradual thinning design for a durable but moldable frame. The hinge may include an unloader pad plate and use Varus/valgus Allen telescoping technology for enhanced degrees of correction after pre molding and curing frame to patient native neutral alignment. A swivel calf strap connection may be provided for comfortable fitting for all calf sizes with a custom slim, anti-slip down "Y" strap. The Y strap (e.g., 710), may have a Y shape with three ends. A first end of the strap may connect to a lower pad plate (e.g., 110) at the front or anterior side of the user's leg (e.g., via connector 715), while the remaining other two ends connect at the side of the lower pad plate 110 corresponding to the posterior side of the user's leg (at connectors 720, 725). In one example, each of these two ends may be configured for adjustment at the connectors 720, 725 to tailor the fit of the Y strap to the particular contours of the user's calf to prevent downward slippage of the brace, among other example advantages and features.

It should be appreciated that the knee brace illustrated in FIG. 7 is shown for example purposes only and that similar plates composed of light-curable material may be utilized in a variety of different orthopedic devices, such as knee braces of different designs, shoulder braces, hip braces, elbow braces, wrist braces, ankle braces, back braces, etc. Such light-cured braces may likewise utilize various straps and connectors to connect the customized pad plates to the limb (e.g., arm or leg) of the user, including the Y strap discussed and shown in FIG. 7, among other examples.

Orthopedic braces utilizing customizable, light-curable pad plates may include members integrally connected to the pad plates to couple the pad plates to hinge or rotational components of the brace device. For instance, such as discussed in one or more example above, a hinge frame member may, itself, be in direct contact with the curable resin material contained with the pad plate mold to permanently couple the hinge frame member to the cured pad plate. In other implementations, a hinge (e.g., via its hinge frame members) may be removably coupled to a light-curable pad plate. This may be advantageous in allowing a fault hinge member to be replaced and customized, light-cured pad plates to be reused with a replacement hinge member, by detaching the faulty hinge member from the pad plates and attaching the replacement hinge member to the pad plates in its plates. Similarly, as a user's body grows, atrophies, or otherwise changes in shape or size over time, the cured pad plates may no longer fit as snugly or comfortably as when the pad plates were originally (previously) formed around the limb of the user and cured. Accordingly, a hinge member coupled to the outgrown pad plates may be reused with new pad plates, which may be refit to the user's current body and then attached to the original hinge member, among other example uses. Such detachable implementations may incorporate an attachment member on the pad plates to allow hinge frame members (of a hinge member) to be removably attached to the pad plates at the attachment member, among other examples.

Figure 8A:
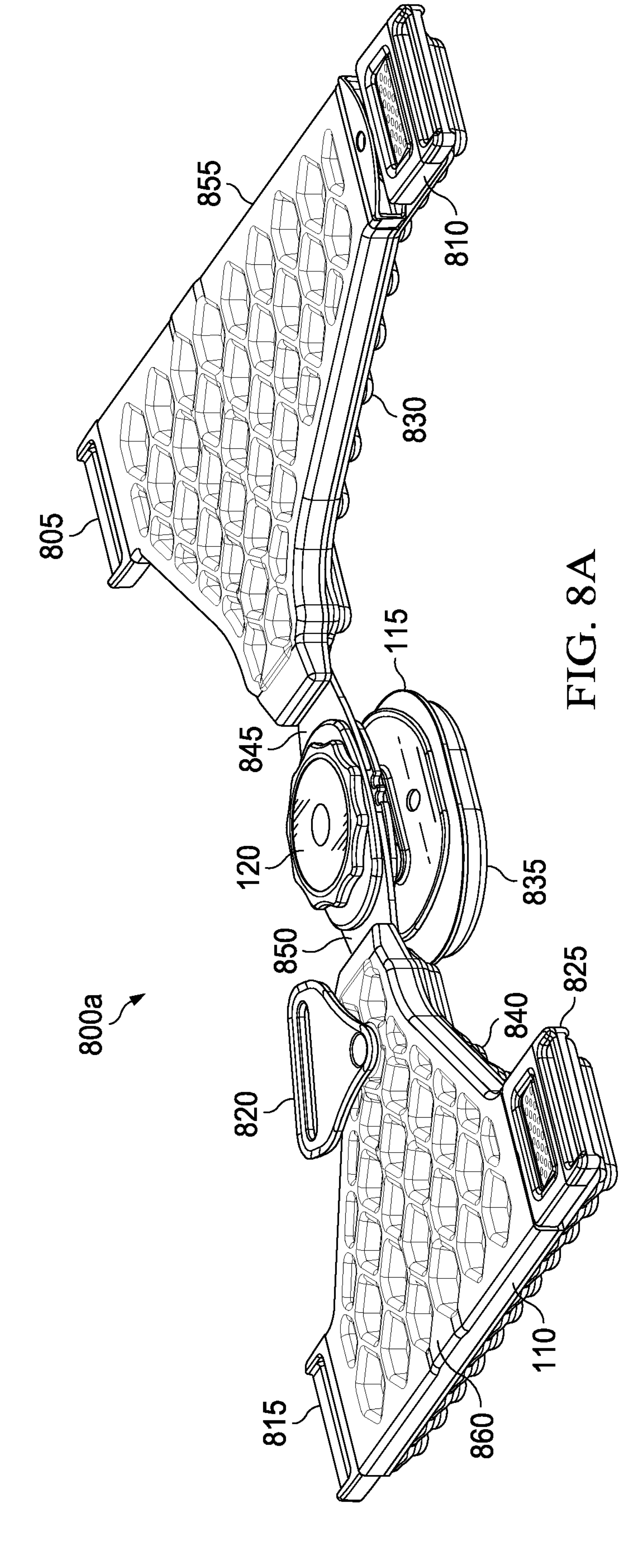
FIGS. 8A-8E illustrate views and features of an example orthopedic brace that includes pad plates configured to be removably attached to a hinge of the brace in accordance with at least one embodiment.

Turning to FIGS. 8A-8E, an example implementation of an orthopedic brace is illustrated that includes pad plates (e.g., 105, 110) configured to be removably attached to hinge frame members (e.g., 845, 850) of an example brace hinge member (e.g., 120). FIG. 8A shows a first perspective view 800*a* of an example brace device including upper (e.g., 105) and lower (e.g., 110) pad plates, which include respective mold components (e.g., 855, 860), which are to contain a light-curable resin within a flexible and at least semi-transparent mold body, as in the other examples discussed herein. The perspective view 800*a* shows the exterior side of the hinge (e.g., the side that will not be in contact or adjacent to the user's limb). Padding (e.g., 830, 840) may be attached to the other side of each pad plate (e.g., 105, 110) representing the side of the pad plate that is to contact the user's body. In some implementations, the brace may include a hinge member 120 with Varus/valgus Allen telescoping capabilities (e.g., to bring pad plate 115 and corresponding padding 835 into contact with the side of the user's knee (or elbow or hip (in the case of an elbow or hip brace), etc.)), among other example features.

Figure 8B:
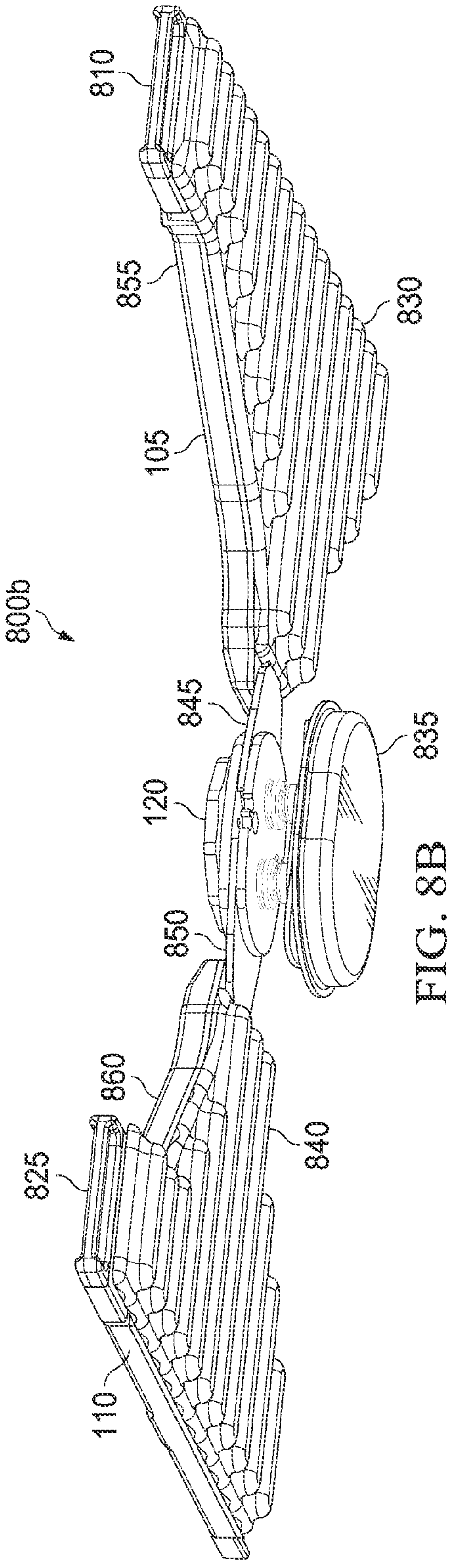
Figure 8C:
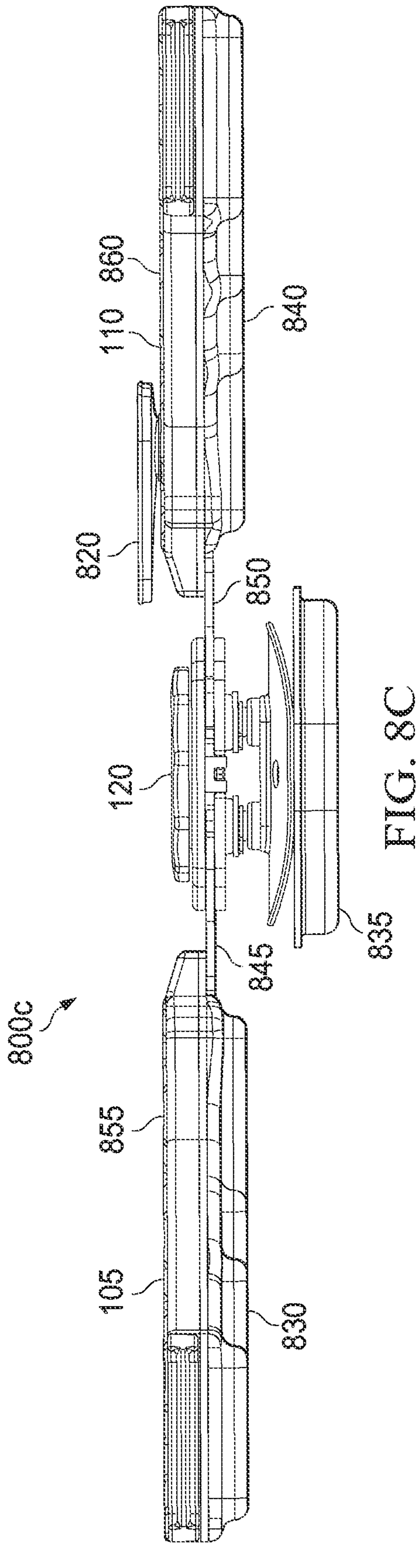

Strap connectors 805, 810, 815, 820, 825 may be connected to pad plates 105, 110 of an example brace, to allow coupling of straps to the pad plates to facilitate connection of the brace to the user's limb. Some of the strap connectors may be configured for movement or adjustment, for instance, through an integrated hinge or swivel. For instance, connector 810 may be configured to swivel or rock to facilitate adjustment of the strap on the upper leg of the user. Connector 820 may be provided for use with a Y strap and enable various angles at which the top end of the Y strap may engage with the lower pad plate (e.g., 110) of the brace, among other examples. Turning to FIG. 8B, another perspective view 800*b* of the example brace device is shown, highlighting an example interior surface (e.g., the surface to come into contact with the user's limb when the brace is fitted/worn). FIG. 8C shows a side view of the example brace device. It should be appreciated that the views 800*a-c* show a brace device prior to the customizable, light-curable pad plates (or even the hinge frame members) being formed around or otherwise customized to the specific contours of the body of the user.

Figure 8D:
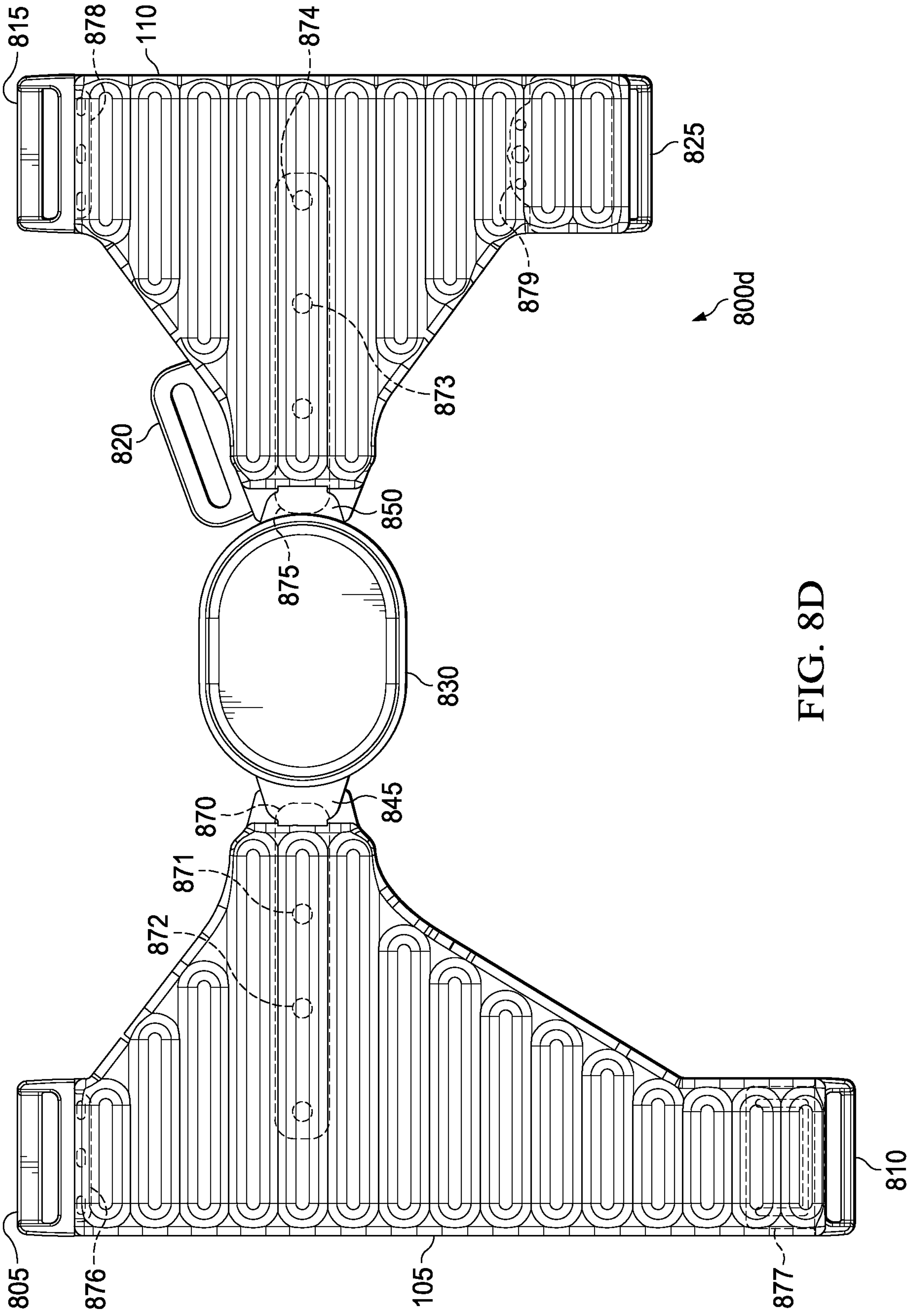

Turning to FIG. 8D, a partially transparent view of the example brace of FIGS. 8A-8C is shown to highlight internal components and features of the brace (e.g., component positioned underneath the padding or internal to or integral with the pad plate mold. For instance, in some implementations, a rigid attachment member (e.g., 870, 875) may be provided that is connected or attached to the pad plate mold. For instance, the rigid attachment member may be adhered to an external surface of the pad plate mold. In other examples, the rigid attachment member (e.g., 870, 875) may be encapsulated in the pad plate mold shell (e.g., embedded within the silicon wall of the mold), sealed in a pocket of the pad plate mold, or otherwise attached to the pad plate mold.

The rigid attachment member may be implemented as rigid plastic or metal member with openings (e.g., 871-874) through which a screw or bolt may be passed to allow corresponding hinge frame members to be removably coupled to the attachment members and fix the hinge to the pad plates. Accordingly, the attachment members (e.g., 870, 875) may be positioned on the pad plate molds to align with (e.g., in parallel) the optimum positioning of the hinge frame members in the brace assembly.

In some implementations, strap connectors (e.g., 805, 810, 815, 820, 825) may also be attached to the pad plates (e.g., 105, 110) using a variety of techniques. In some implementations, one or more of the strap connectors may be integrally formed in the pad plate mold. In some implementations, strap connectors (e.g., 805, 810, 815, 825) may include respective members (e.g., 876, 877, 878, 879), which may be inserted into and sealed to the pad plate molds such that the light-curable resin contacts and flow in and around the members (e.g., via holes, ridges, scalloping, etc. in the member), such that when the pad plates are exposed to light and cured, the strap connector is permanent affixed to the pad plate, among other example attachment techniques. In some implementations, such as implementations of a brace including a Y strap and Y strap connector (e.g., 820), the strap connector may be coupled to a pad plate (e.g., 110) by bolting or otherwise attaching the strap connector member to the attachment member (e.g., 875) of the pad plate, among other example features and implementations.

Figure 8E:
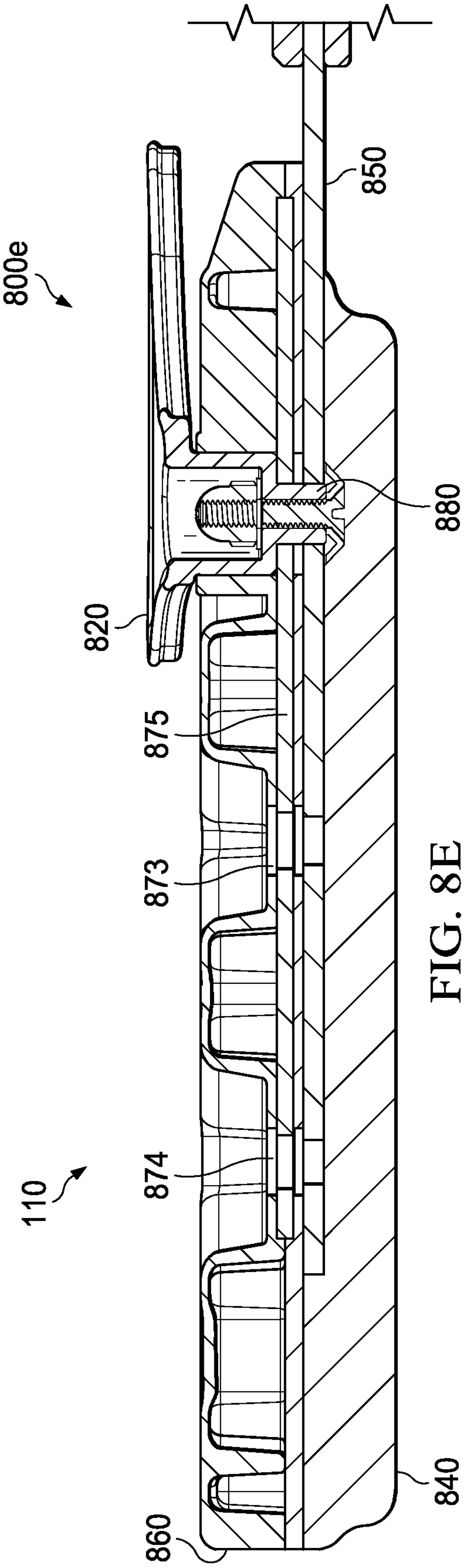

FIG. 8E is a cross-sectional view 800*e* of an example pad plate (e.g., 110) including an integrated rigid attachment member 875. The rigid attachment member 875 may be appreciably more rigid (e.g., of a different material) than the material used to implement the pad plate mold (e.g., 860), which is to be filled with the light-curable resin. In the example of FIG. 8E, the rigid attachment member 875 is attached to and encapsulated within the pad plate mold (e.g., attached to an interior surface of the pad plate mold or encapsulated within a wall of the pad plate mold). A hinge frame member (e.g., 850) may be positioned to align within the attachment member 875 and attached to the attachment member 875 (e.g., using screws, bolts, or other attachment mechanisms) to form a rigid attachment between the pad plate and the hinge of the brace assembly. Accordingly, corresponding holes or openings (e.g., 874, 875, 880, etc.) may be provided on each of the attachment member 875 and the corresponding hinge frame member to facilitate the passage/insertion of these attachment mechanisms. Some openings (e.g., 880) may be used to couple other brace components (e.g., strap connector 820) to the pad plate (in addition to the hinge frame member). The padding (e.g., 840), in some implementations, may be attached to the pad plate after the hinge frame member (e.g., 850) is connected to the attachment member (e.g., 875) to overlay the padding over the hinge frame member 850.

Prior to curing of the pad plate bodies (e.g., by exposure to UV light energy) the attachment member 875 may represent the only rigid portion of the pad plate(s). This rigidity enables a structurally sound connection of the pad plate bodies to the hinge of the brace assembly. With the pad plate bodies attached to the brace hinge, the brace assembly may be attached to a patient (e.g., by a medical professional) for professional fitting and curing, among other example advantages.

Figure 9A:
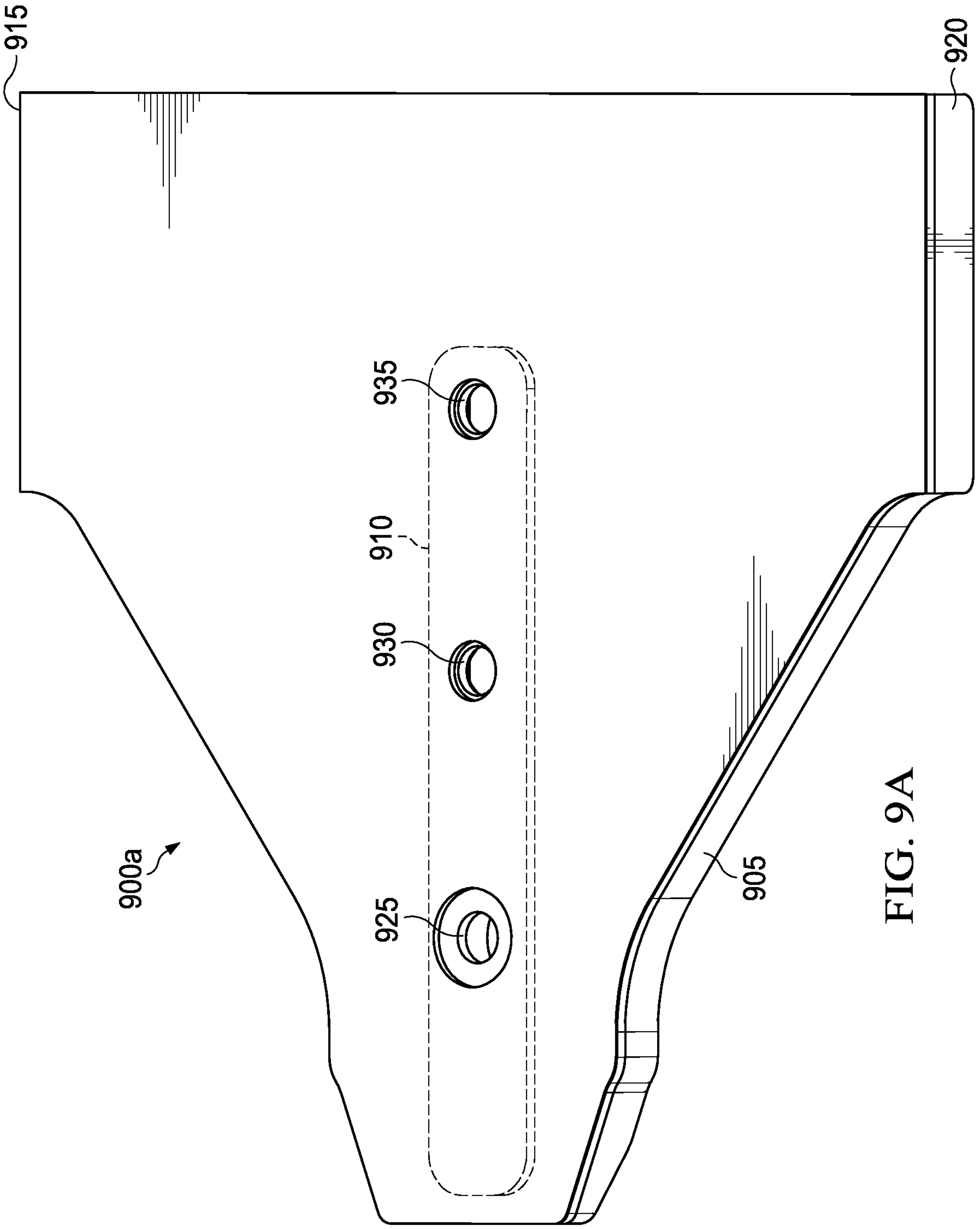
FIGS. 9A-9C illustrate views of an example pad plate shell including a rigid attachment member in accordance with at least one embodiment.
Figure 9B:
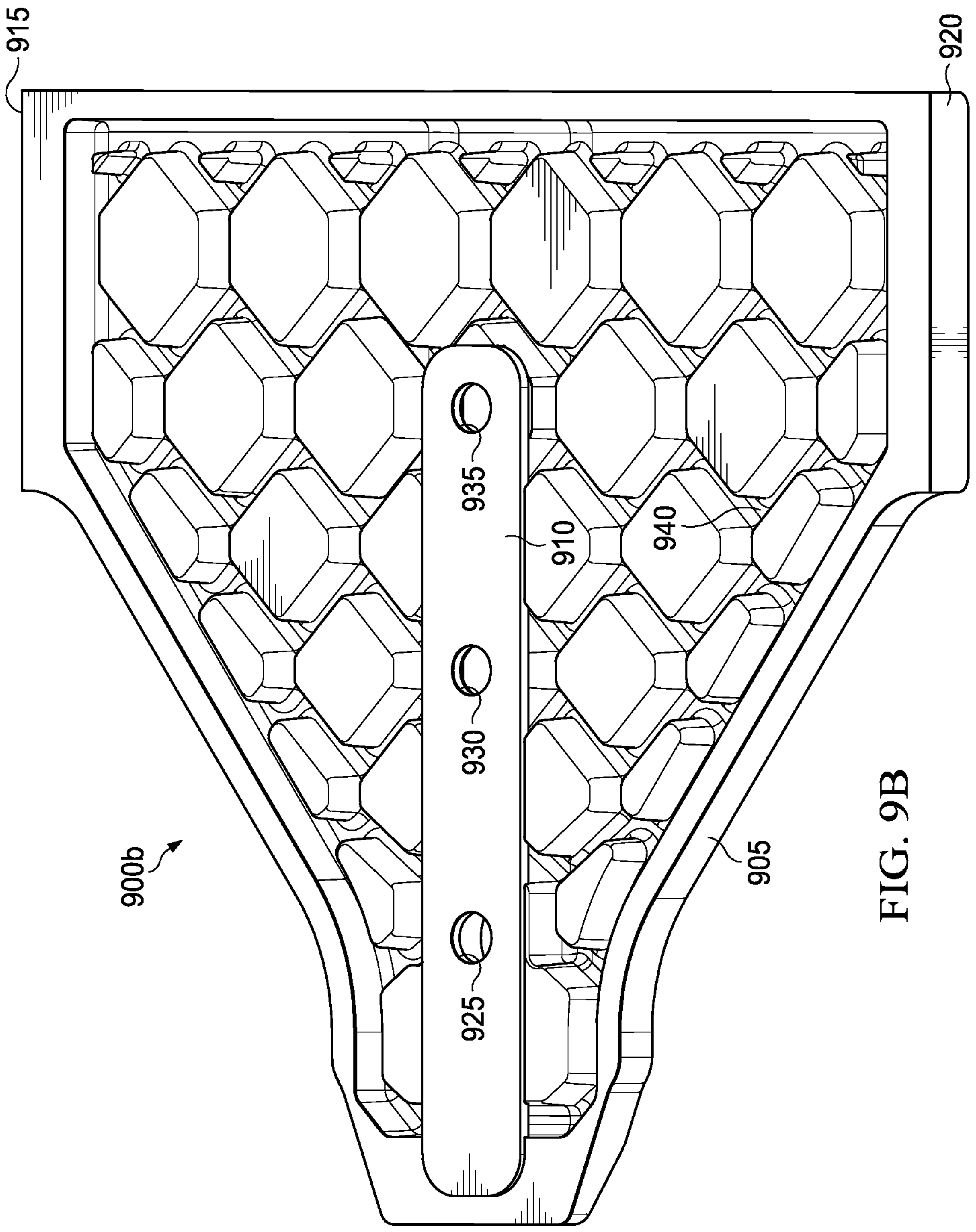
Figure 9C:
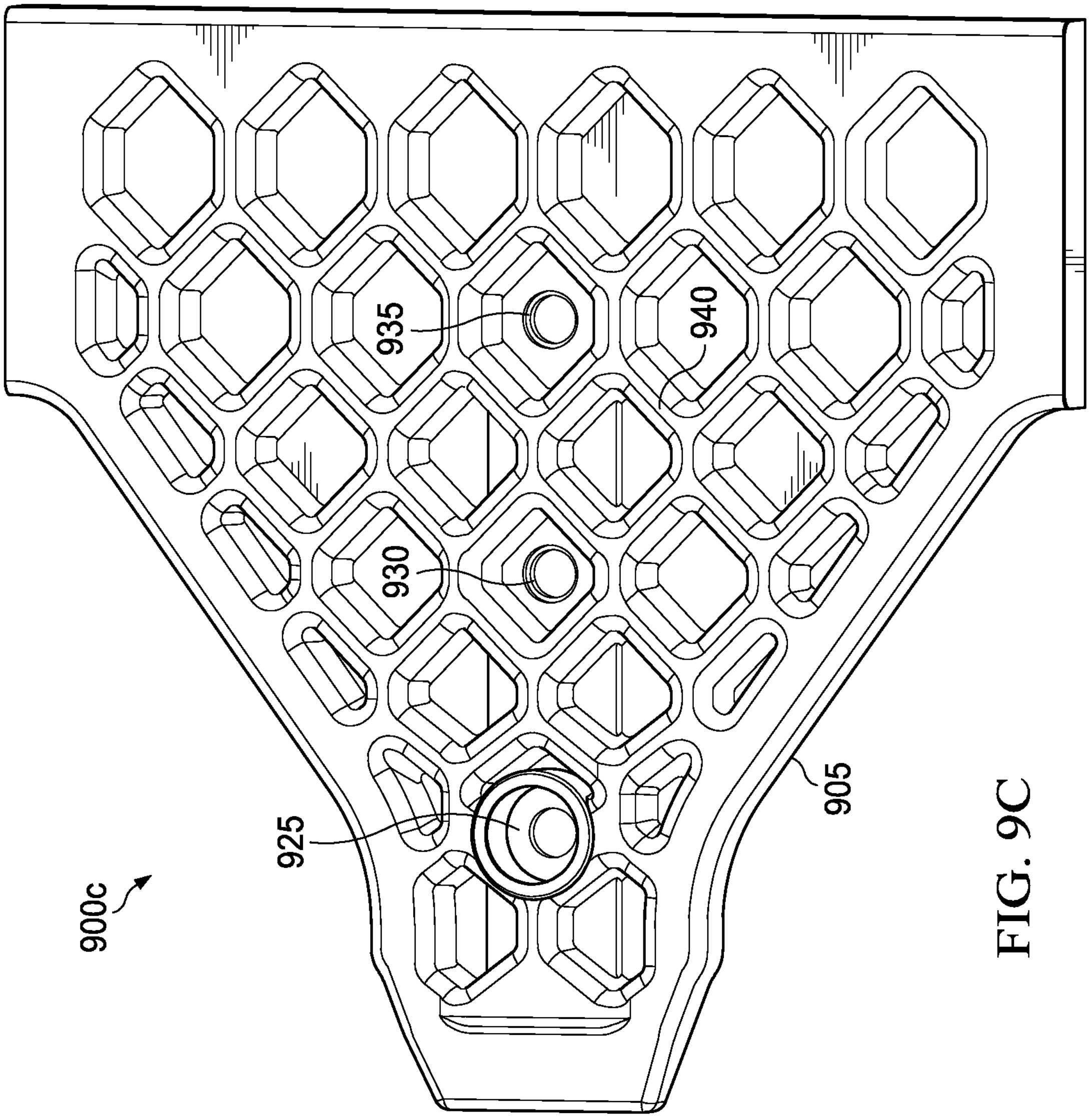

FIGS. 9A-9C illustrate views 900*a*-*c* of an example pad plate mold 905, which include a rigid attachment member 910 and which may be filled with light-curable resin for use in constructing an orthopedic brace assembly (e.g., a hip brace, knee brace, elbow brace, ankle brace, wrist brace, shoulder brace, etc.). the pad plate mold 905 may, in some implementations, may include openings or other features to enable the attachment of strap connectors (e.g., at ends 915, 920) of the pad plate, among other example features. FIG. 9A shows an outline of an example attachment member 910 attached within the pad plate mold 905. FIG. 9B includes a cut-away view 900*b* (with a wall or outer surface of the pad plate mold removed or invisible within the view 900*b*) to show the positioning of the example attachment member 910 within the pad plate mold 905. As discussed above, in some implementations, the pad plate (and pad plate mold (which forms an external surface of the pad plate)) may be formed as a lattice of interconnected channels formed by the mold, with the light-curable resin filling the channels (e.g., 940). The attachment member may be adhered to or encapsulated, at least partially, within the mold material (e.g., added to a mold used to form the pad plate mold, where the material used to form the pad plate mold (e.g., a transparent silicon rubber) at least partially surrounds the attachment member and is cured to permanently join the attachment member (e.g., 910) to the pad plate mold), among other example implementations.

As introduced above, a rigid attachment member 910 may include one or more openings or other attachment mechanisms (e.g., latches, hooks, etc.) to enable other components or parts of an orthopedic brace to be attached to the corresponding pad plate to construct or enhance the orthopedic brace. For instance, openings (e.g., 925, 930, 935) may be provided, which are adapted to accept a screw, a rivet, or other fastener. These openings (e.g., 925, 930, 935) may be further formed and positioned to align with two or more corresponding openings provided on a hinge frame member to facilitate attachment of the hinge to the pad plate. These openings (e.g., 925, 930, 935), in some implementations, may likewise pass through the pad plate mold material (e.g., with these openings in the pad plate mold sealed to prevent escape of light-curable resin contained with the mold). In some implementations, the openings may correspond with openings provided in the geometry of the pad plate mold (e.g., openings formed by the lattice-like structure of the pad plate mold (such as illustrated in FIG. 9C, showing a reverse side of the pad plate illustrated in FIG. 9A)), among other example implementations.

In some implementations, at least a portion of an example attachment member 910 may be exposed (e.g., within the internal cavity of the pad plate mold) to and in contact with light-curable resin contained within the pad plate mold. In such implementations, the coupling of the attachment member to the remaining pad plate may be reinforced within the pad plate following curing of the light-curable resin. In some cases, the geometry of the attachment member may be augmented or configured to encourage such reinforced coupling (e.g., by adopting geometries and features similar to those illustrated for example frame members in FIGS. 4A-4E).

While the examples of FIGS. 8A-9C illustrate an example attachment member (e.g., 910) as an elongated or rectangular plate member, it should be appreciated that other implementations of an attachment member may adopt other geometries (e.g., triangular, trapezoidal, irregular geometries, etc.), for instance, based on the types of components (e.g., hinge attachments, strap connectors, etc.) the attachment member is to be coupled with to construct the corresponding orthopedic brace.

Figure 10:
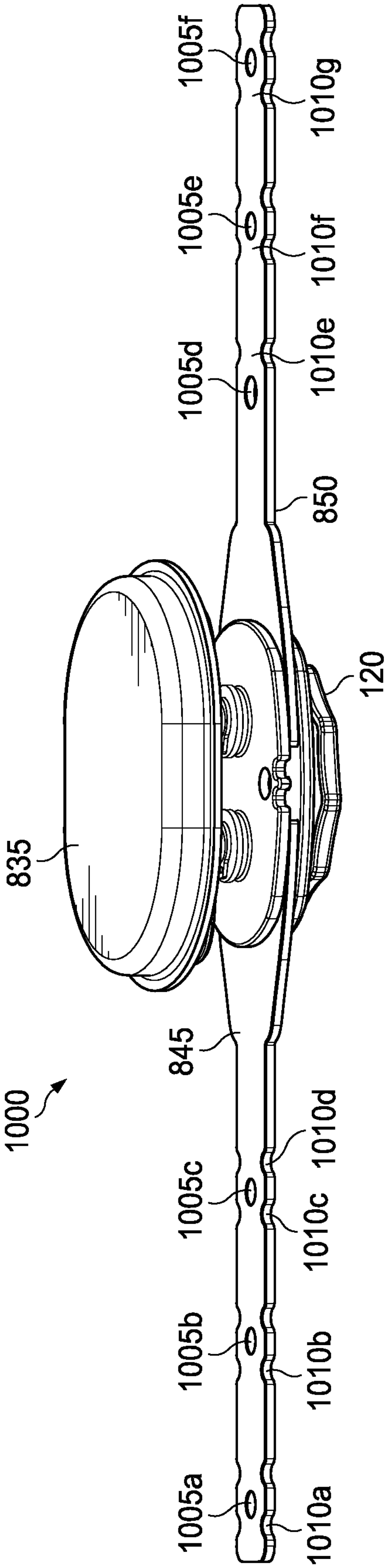
FIG. 10 illustrates an example hinge component of an orthopedic brace in accordance with at least one embodiment.

Turning to FIG. 10, an illustration 1000 of an example hinge component 120 is shown as separate from a remaining orthopedic brace assembly. The hinge may include mechanical components to facilitate controlled swiveling, rotation, pivoting, or other controlled movement designated for the brace. In some implementations, additional padding may be provided, such as on an unloader plate (e.g., 835) in a knee brace implementation, among other examples. The hinge component may additionally include one or more frame members (e.g., 845, 850), which are configured to connect to other portions of the brace, such as padding, wrap or strap elements, or other components. One or more of these frame members may be configured to couple to a pad plate formed from light-cured material, such as discussed above. Indeed, frame members (e.g., 845, 850) may be formed to align with and connect to attachment members coupled to or formed in the pad plates (e.g., through openings 1005*a-c* or 1005*d-f*). While frame members (e.g., 845, 850) may be formed from rigid materials to provide mechanical strength in the brace, in some implementations, nonuniformities may be incorporated within the frame members to facilitate some directed manipulation and bending of the members to form the frame members to the contours of the patient's body. For instance, notches (e.g., 1010*a-g*) may be provided at certain points along the frame members (e.g., 845, 850), such as near connection points (e.g., 1005*a-f*) on the members used to couple the hinge component to pad plates or other components of the brace, among other example implementations.

Figure 11:
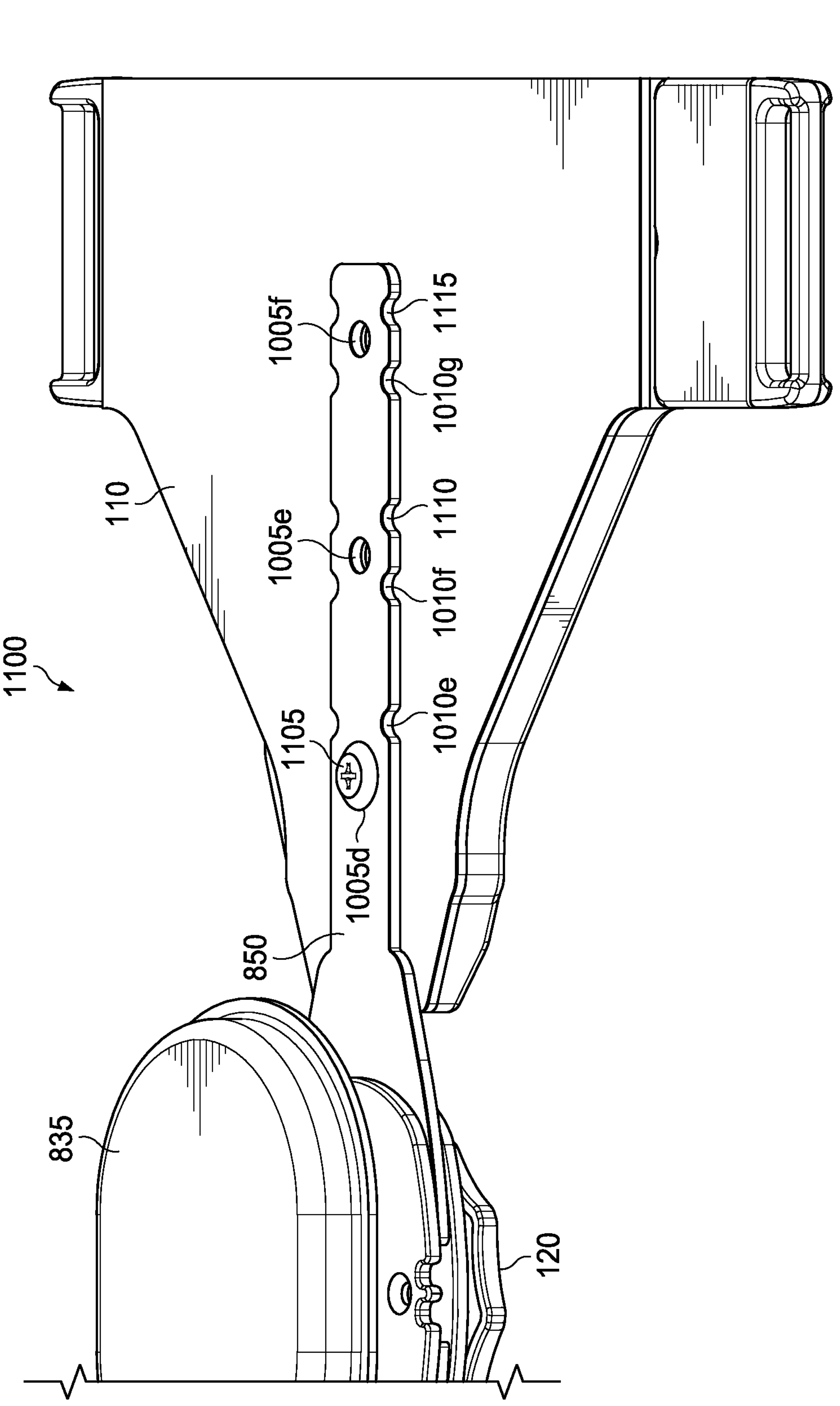
FIG. 11 illustrates the example connection of an example hinge component of an orthopedic brace to a rigid attachment member of a pad plate of the orthopedic brace in accordance with at least one embodiment.

Turning to FIG. 11, an illustration 1100 is provided showing the attachment of an example frame member (e.g., 850) to an example pad plate (e.g., 110) at an attachment member (not visible) embedded within the pad plate 110, such as an attachment member similar to that illustrated in the example of FIGS. 9A-9C. A screw, bolt, rivet, or other hardware (e.g., 1105) may be passed through the opening(s) (e.g., 1005*d*) of the frame member and the corresponding opening provided on the pad plate 110 and passing through the attachment member embedded within or attached to the pad plate and secured to removably couple the frame member (e.g., 850) and the hinge 120 itself to the pad plate 110. In some cases, two or more such points of attachment may be secured between the hinge frame member and a pad plate.

Figure 12B:
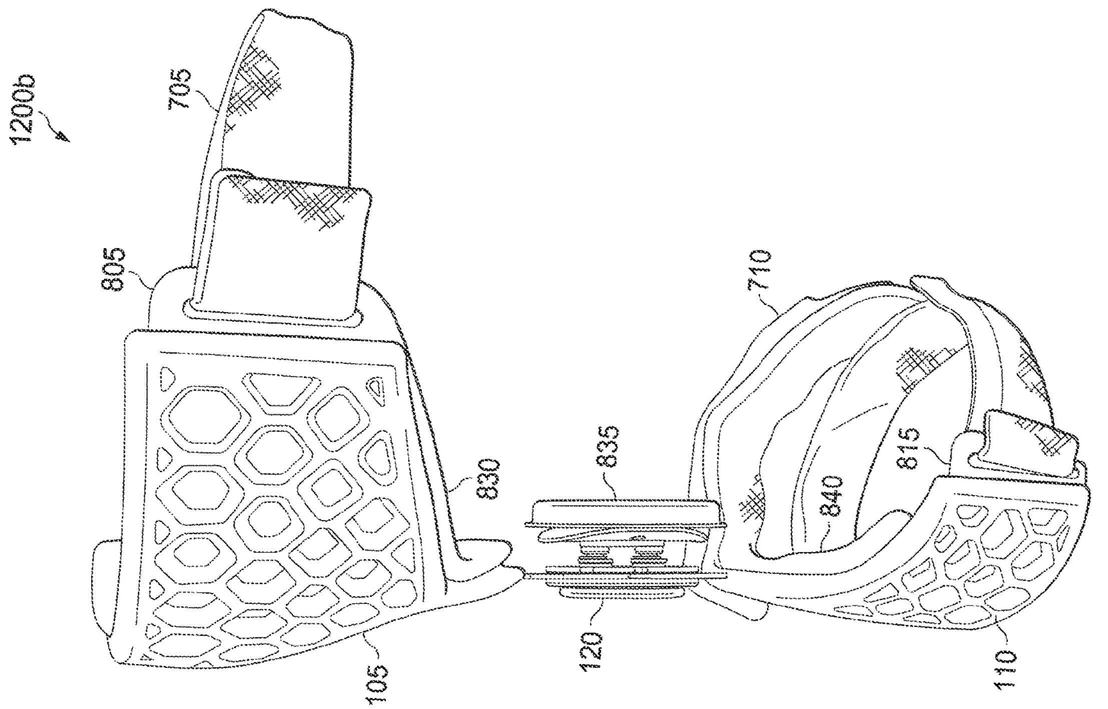
FIG. 12B illustrates an example customizable orthopedic brace in accordance with at least one embodiment.
Figure 12A:
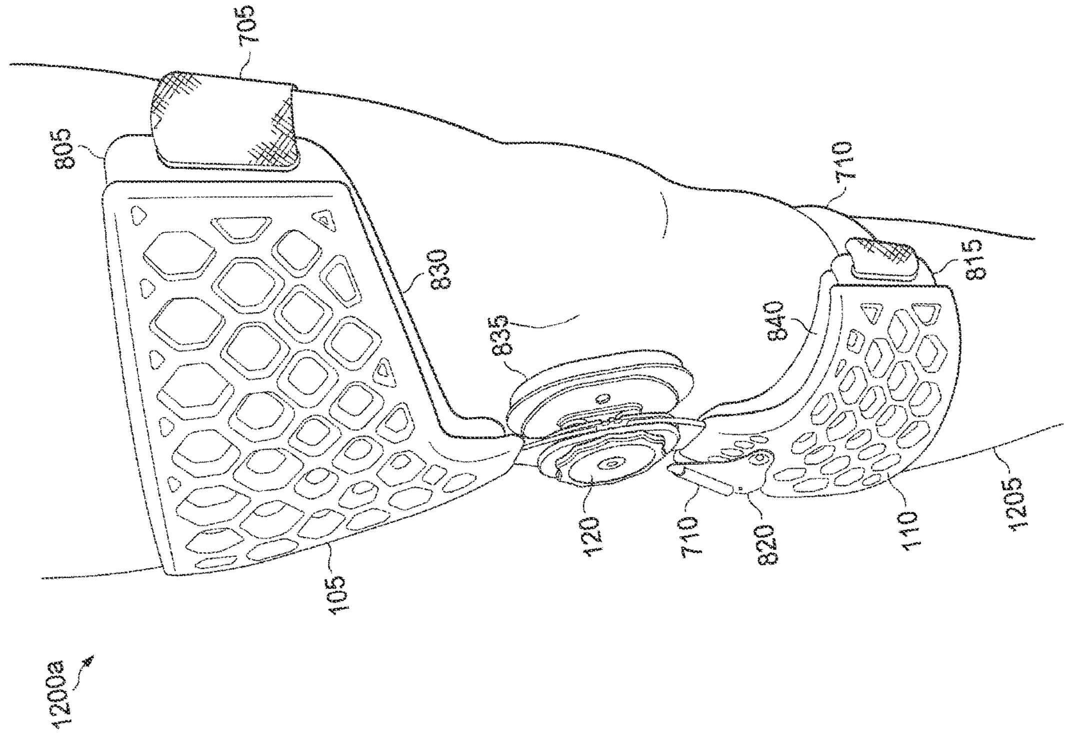
FIG. 12A illustrates the example use of an example customizable orthopedic brace in accordance with at least one embodiment.

FIGS. 12A-12B are images 1200*a-b* illustrating the example fitting and use of an example knee brace. In this particular example, a knee brace may include two pad plate elements (e.g., an upper pad plate 105 and a lower pad plate 110), each composed of a silicon mold or bladder containing light-curable resin. In this example, a hinge component 120 may be provided and may be coupled to each of the pad plate molds by removably coupling frame members of the hinge 120 to respective attachment members embedded or otherwise attached to the pad plate bladders or molds, such as discussed in some of the example embodiments disclosed herein. Strap connectors (e.g., 805, 815, 820, etc.) may be provided through which straps (e.g., 705, 710) may be connected to ends of the pad plates, to strap the brace to the leg 1205 of a user-patient.

In one example implementation, the brace may be custom-fit to the body of a patient by attaching the uncured pad plate components to a hinge component. Straps may be preassembled connected to the pad plate may be additionally attached to the respective pad plates. Prior to curing the pad plates may be particularly flexible and malleable, such that they can be wrapped around the limb(s) (or other body parts) of a user in a form-fitting manner. With the pad plates wrapped around the user and the brace situated in the optimal position (e.g., by a trained medical professional), a UV light source may be applied to the pad plates (while they are strapped to the subject patient-user) to cure the pad plates to permanently keep the form-fit shape. After curing, the brace may be removed from the patient-user and represent a custom-fit brace (such as illustrated in FIG. 12B), which the same user-patient may use in connection with treatment or support of the affected joint and/or limb, It should be appreciated that while some of the examples shown and illustrated refer specifically to a knee brace, the principles discussed above may be applied equally to other brace types which include one or more pads/plates coupled to one or more hinges or controlled movement mechanisms. Examples of such braces may include, for instance, elbow braces, hip braces, shoulder braces, wrist braces, and ankle braces. These concepts and solutions may also be applied to bracing solutions for animals (e.g., in veterinary medicine), among other example implementations of these principles.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

Example 1 is an orthopedic brace including: one or more pad plates formed of a light-curable material; and a hinge including one or more hinge framework elements connected to the one or more pad plates.

Example 2 includes the subject matter of example 1, where light-curable material includes an ultraviolet-light-curable resin.

Example 3 includes the subject matter of any one of examples 1-2, further including a mold formed from a flexible material, where the mold contains the light-curable material and forms an exterior surface of the one or more pad plates.

Example 4 includes the subject matter of example 3, where the mold includes a sheath to accept the hinge framework element, and the sheath is to be infused with the light curable material when the hinge framework element is within the sheath.

Example 5 includes the subject matter of example 4, where the one or more hinge framework elements are integrally connected to the one or more pad plates during curing of the light-curable material.

Example 6 includes the subject matter of example 5, where one or more hinge framework elements include nonuniformities to encourage binding of the one or more hinge framework elements to the light-curable material after curing.

Example 7 includes the subject matter of example 6, where the nonuniformities include one or more of: projections from a respective face of the hinge framework element; depressions in a face of the hinge framework element; holes in the hinge framework element; or irregular edges of the hinge framework element.

Example 8 includes the subject matter of example 3, where at least a particular one of the pad plates includes a rigid attachment member, the rigid attachment member is connected to the mold of the particular pad plate, and the hinge framework is to couple to the particular pad plate via the rigid attachment member.

Example 9 includes the subject matter of example 8, where the rigid attachment member is made of a first material, and the mold is made of a second material less rigid than the first material.

Example 10 includes the subject matter of example 9, where the rigid attachment member is at least partially contained within the exterior mold.

Example 11 includes the subject matter of any one of examples 3-10, where the mold includes one or more strap connectors.

Example 12 includes the subject matter of example 11, where one or more strap connectors includes three strap connectors to accept three ends of a Y-shaped strap.

Example 13 includes the subject matter of any one of examples 3-12, where the mold is formed from a silicon-based material.

Example 14 includes the subject matter of any one of examples 1-13, where the brace includes one of a knee brace, elbow brace, should brace, hip brace, back brace, wrist brace, shoulder brace, or ankle brace.

Example 15 is an apparatus including: a pad plate for use in an orthopedic brace, where the pad plate includes: an exterior shell, where the exterior shell is made of an elastomeric material, and the exterior shell is to contain a light-curable material; and a rigid attachment member connected to the pad plate mold, where the attachment member is configured to couple to a frame member of the orthopedic brace.

Example 16 includes the subject matter of example 15, where the pad plate further includes one or more strap connectors to connect straps to the pad plate, where the straps are to couple the pad plate to a limb of a user.

Example 17 includes the subject matter of any one of examples 15-16, where the rigid attachment member is at least partially embedded in the elastomeric material of the exterior shell to couple the rigid attachment member to the exterior shell.

Example 18 is a method including: connecting a pad plate to a hinge element of an orthopedic brace, where the pad plate includes an elastomeric shell containing a light-curable material; wrapping the pad plate around a limb of a user; and applying ultraviolet light to the pad plate to cure the light-curable material and permanently fix the shape of the pad plate to correspond to the limb of the user.

Example 19 includes the subject matter of example 18, where the pad plate further includes a rigid attachment member coupled to the elastomeric shell, and the pad plate is connected to the hinge element at the rigid attachment member.

Example 20 includes the subject matter of example 18, further including injecting the light-curable material into the elastomeric shell.

Example 21 includes the subject matter of any one of examples 18-20, where the method includes a method for making the orthopedic brace.

Example 22 includes the subject matter of example 21, where the orthopedic brace includes the orthopedic brace of any one of examples 1-14.

Example 23 includes an orthopedic device constructed by the method of any one of examples 18-20.

A detailed description has been given with reference to specific exemplary embodiments. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

The invention claimed is:

1. An orthopedic brace comprising:

one or more pad plates comprising a mold formed from a flexible material, wherein the mold comprises one or more hollow, tubular cavities, wherein the one or more tubular cavities are configured to contain a light-curable fluid, and the flexible material is configured to allow passage of light into the one or more tubular cavities to cure the light-curable fluid; and a hinge comprising one or more hinge framework elements connected to the one or more pad plates.

2. The orthopedic brace of claim 1, wherein the mold contains the light-curable material and forms an exterior surface of the one or more pad plates.

3. The orthopedic brace of claim 2, wherein a first one of the one or more pad plates comprises a rigid attachment member, the rigid attachment member is connected to the mold of the first pad plate, and the hinge framework is to couple to the first pad plate via the rigid attachment member.

4. The orthopedic brace of claim 3, wherein the rigid attachment member is made of a first material, and the mold is made of a second material less rigid than the first material.

5. The orthopedic brace of claim 2, wherein the mold comprises one or more strap connectors.

6. The orthopedic brace of claim 5, wherein one or more strap connectors comprises three strap connectors to accept three ends of a Y-shaped strap.

7. The orthopedic brace of claim 2, wherein the mold comprises a sheath to accept the hinge framework element, and the sheath is to be infused with the light-curable material when the hinge framework element is within the sheath to integrally fasten the hinge framework element to a corresponding one of the one or more pad plates when light is applied to cure the light-curable material.

8. The orthopedic brace of claim 2, wherein the mold is formed from a silicon-based material.

9. The orthopedic brace of claim 1, wherein the one or more hollow, tubular cavities form a perimeter of the mold and one or more openings in the mold within the perimeter.

10. The orthopedic brace of claim 9, wherein one or more hinge framework elements comprise nonuniformities to encourage binding of the one or more hinge framework elements to the light-curable material after curing.

11. The orthopedic brace of claim 10, wherein the nonuniformities comprise one or more of:

projections from a respective face of the hinge framework element;

depressions in a face of the hinge framework element;

holes in the hinge framework element; or irregular edges of the hinge framework element.

12. The orthopedic brace of claim 1, wherein light-curable material comprises an ultraviolet-light-curable resin.

13. The orthopedic brace of claim 1, wherein the orthopedic brace comprises one of a knee brace, elbow brace, hip brace, back brace, wrist brace, shoulder brace, or ankle brace.

14. An apparatus comprising:

a pad plate for use in an orthopedic brace, wherein the pad plate comprises:

an exterior shell, wherein the exterior shell is made of an elastomeric material, the exterior shell comprises one or more tubular cavities, and the one or more tubular cavities are configured to contain a light-curable material; and a rigid attachment member connected to the pad plate mold, wherein the attachment member is configured to couple to a frame member of the orthopedic brace.

15. The apparatus of claim 14, wherein the pad plate further comprises one or more strap connectors to connect straps to the pad plate, wherein the straps are to couple the pad plate to a limb of a user.

16. The apparatus of claim 14, wherein the rigid attachment member is at least partially embedded in the elastomeric material of the exterior shell to couple the rigid attachment member to the exterior shell.

17. A method comprising:

connecting a pad plate to a hinge element of an orthopedic brace, wherein the pad plate comprises an elastomeric shell comprising one or more tubular cavities configured to contain a light-curable material, wherein the elastomeric shell is adapted to allow passage of light into the one or more tubular cavities;

wrapping the pad plate around a limb of a user; and applying ultraviolet light to the pad plate to cure the light-curable material and permanently fix the shape of the pad plate to correspond to the limb of the user.

18. The method of claim 17, wherein the pad plate further comprises a rigid attachment member coupled to the elastomeric shell, and the pad plate is connected to the hinge element at the rigid attachment member.

19. The method of claim 17, further comprising injecting the light-curable material into the elastomeric shell.

* * * * *